United States Patent
Rowe et al.

(10) Patent No.: US 9,301,749 B2
(45) Date of Patent: Apr. 5, 2016

(54) EXPANDABLE CLIP FOR TISSUE REPAIR

(71) Applicant: Edwards Lifesciences Corporation, Irvine, CA (US)

(72) Inventors: Stanton J. Rowe, Newport Coast, CA (US); David L. Hauser, Newport Beach, CA (US); Rafael Pintor, Mission Viejo, CA (US); Richard B. Cates, Hermosa Beach, CA (US)

(73) Assignee: Edwards Lifesciences Corporation, Irvine, AZ (US)

( * ) Notice: Subject to any disclaimer, the term of this patent is extended or adjusted under 35 U.S.C. 154(b) by 0 days.

(21) Appl. No.: 14/337,155

(22) Filed: Jul. 21, 2014

(65) Prior Publication Data

US 2014/0336702 A1 Nov. 13, 2014

Related U.S. Application Data

(63) Continuation of application No. 11/635,095, filed on Dec. 7, 2006, now abandoned.

(60) Provisional application No. 60/843,267, filed on Sep. 8, 2006.

(51) Int. Cl.
  *A61B 17/04* (2006.01)
  *A61B 17/00* (2006.01)
  *A61B 17/06* (2006.01)

(52) U.S. Cl.
  CPC .......... *A61B 17/0487* (2013.01); *A61B 17/0057* (2013.01); *A61B 17/0469* (2013.01); *A61B 17/0482* (2013.01); *A61B 17/0483* (2013.01); *A61B 17/06166* (2013.01); *A61B 2017/0061* (2013.01); *A61B 2017/00243* (2013.01); *A61B 2017/00575* (2013.01); *A61B 2017/00654* (2013.01); *A61B 2017/0445* (2013.01); *A61B 2017/0456* (2013.01); *A61B 2017/0464* (2013.01); *A61B 2017/0488* (2013.01); *A61B 2017/0496* (2013.01)

(58) Field of Classification Search
  CPC .......... A61B 17/0487; A61B 17/0496; A61B 17/0482; A61B 2017/0057; A61B 2017/00575; A61B 2017/0061; A61B 2017/00615; A61B 2017/00619; A61B 2017/0496; A61B 2017/00659; A61B 2017/00663
  See application file for complete search history.

(56) References Cited

U.S. PATENT DOCUMENTS

| | | | |
|---|---|---|---|
| 3,769,980 A | 11/1973 | Karman | |
| 3,805,793 A | 4/1974 | Wright | |
| 4,350,160 A | 9/1982 | Kolesov et al. | |

(Continued)

FOREIGN PATENT DOCUMENTS

| | | |
|---|---|---|
| DE | 19725739 | 4/1999 |
| EP | 570915 | 11/1993 |

(Continued)

*Primary Examiner* — Alexander Orkin

(57) ABSTRACT

An apparatus, system, and method for repairing openings such as septal defects includes advancing a catheter to the site of the defect, grasping opposing edges of the defect, passing one or more suture lines through the opposing edges, tightening the suture lines, and deploying and expanding a fastener to secure the suture lines and close the defect. The fastener can include tissue-growth-inducing materials to encourage tissue growth onto or into the fastener and/or suture. The fastener includes a locking clip portion and a plug portion, which may be an expandable portion and/or tissue-growth-inducing portion.

15 Claims, 25 Drawing Sheets

(56) References Cited

U.S. PATENT DOCUMENTS

| | | |
|---|---|---|
| 5,080,663 A | 1/1992 | Mills et al. |
| 5,242,456 A | 9/1993 | Nash et al. |
| 5,267,958 A | 12/1993 | Buchbinder et al. |
| 5,330,442 A | 7/1994 | Green et al. |
| 5,374,275 A | 12/1994 | Bradley et al. |
| 5,403,326 A | 4/1995 | Harrison et al. |
| 5,443,446 A | 8/1995 | Shturman |
| 5,458,131 A | 10/1995 | Wilk |
| 5,474,573 A | 12/1995 | Hatcher |
| 5,540,704 A | 7/1996 | Gordon et al. |
| 5,569,274 A | 10/1996 | Rapacki et al. |
| 5,573,540 A | 11/1996 | Yoon |
| 5,575,800 A | 11/1996 | Gordon |
| 5,578,044 A | 11/1996 | Gordon et al. |
| 5,601,574 A | 2/1997 | Stefanchik et al. |
| 5,609,598 A | 3/1997 | Laufer et al. |
| 5,662,664 A | 9/1997 | Gordon et al. |
| 5,662,681 A | 9/1997 | Nash et al. |
| 5,669,935 A | 9/1997 | Rosenman et al. |
| 5,685,867 A | 11/1997 | Twardowski et al. |
| 5,695,457 A | 12/1997 | St. Goar et al. |
| 5,700,272 A | 12/1997 | Gordon et al. |
| 5,713,910 A | 2/1998 | Gordon et al. |
| 5,713,911 A | 2/1998 | Racenet et al. |
| 5,716,367 A | 2/1998 | Koike et al. |
| 5,741,277 A | 4/1998 | Gordon et al. |
| 5,741,279 A | 4/1998 | Gordon et al. |
| 5,766,183 A | 6/1998 | Sauer |
| 5,792,094 A | 8/1998 | Stevens et al. |
| 5,792,153 A | 8/1998 | Swain et al. |
| 5,810,847 A | 9/1998 | Laufer et al. |
| 5,814,097 A | 9/1998 | Sterman et al. |
| 5,836,956 A | 11/1998 | Buelna et al. |
| 5,839,639 A | 11/1998 | Sauer et al. |
| 5,849,019 A | 12/1998 | Yoon |
| 5,860,992 A | 1/1999 | Daniel et al. |
| 5,885,238 A | 3/1999 | Stevens et al. |
| 5,891,159 A | 4/1999 | Sherman et al. |
| 5,891,160 A | 4/1999 | Williamson et al. |
| 5,924,424 A | 7/1999 | Stevens et al. |
| 5,928,224 A | 7/1999 | Laufer |
| 5,928,250 A | 7/1999 | Koike et al. |
| 5,968,059 A | 10/1999 | Ellis et al. |
| 5,972,020 A | 10/1999 | Carpentier et al. |
| 5,976,159 A | 11/1999 | Bolduc et al. |
| 6,004,310 A | 12/1999 | Bardsley et al. |
| 6,010,531 A | 1/2000 | Donlon et al. |
| 6,015,417 A | 1/2000 | Reynolds, Jr. |
| 6,015,427 A | 1/2000 | Mueller et al. |
| 6,029,671 A | 2/2000 | Stevens et al. |
| 6,047,700 A | 4/2000 | Eggers et al. |
| 6,056,760 A | 5/2000 | Koike et al. |
| 6,080,182 A | 6/2000 | Shaw et al. |
| 6,083,219 A | 7/2000 | Laufer |
| 6,088,889 A | 7/2000 | Luther et al. |
| 6,117,159 A | 9/2000 | Huebsch et al. |
| 6,136,010 A | 10/2000 | Modesitt et al. |
| 6,149,660 A | 11/2000 | Laufer et al. |
| 6,157,852 A | 12/2000 | Selmon et al. |
| 6,162,233 A | 12/2000 | Williamson et al. |
| 6,165,183 A | 12/2000 | Kuehn et al. |
| 6,165,204 A | 12/2000 | Levinson et al. |
| 6,190,357 B1 | 2/2001 | Ferrari et al. |
| 6,210,419 B1 | 4/2001 | Mayenberger et al. |
| 6,234,995 B1 | 5/2001 | Peacock |
| 6,269,819 B1 | 8/2001 | Oz et al. |
| 6,312,447 B1 | 11/2001 | Grimes |
| 6,443,922 B1 | 9/2002 | Roberts et al. |
| 6,461,366 B1 | 10/2002 | Seguin |
| 6,494,898 B1 | 12/2002 | Roby et al. |
| 6,508,777 B1 | 1/2003 | Macoviak et al. |
| 6,508,828 B1 | 1/2003 | Akerfeldt et al. |
| 6,575,971 B2 | 6/2003 | Hauck et al. |
| 6,582,388 B1 | 6/2003 | Coleman et al. |
| 6,626,930 B1 | 9/2003 | Allen et al. |
| 6,629,534 B1 | 10/2003 | St. Goar et al. |
| 6,645,205 B2 | 11/2003 | Ginn |
| 6,752,813 B2 | 6/2004 | Goldfarb et al. |
| 6,770,083 B2 | 8/2004 | Seguin |
| 6,875,224 B2 | 4/2005 | Grimes |
| 2002/0049402 A1 | 4/2002 | Peacock et al. |
| 2002/0107531 A1 | 8/2002 | Schreck et al. |
| 2002/0183787 A1 | 12/2002 | Wahr et al. |
| 2003/0130571 A1 | 7/2003 | Lattouf |
| 2003/0167071 A1 | 9/2003 | Martin et al. |
| 2004/0044365 A1 | 3/2004 | Bachman |
| 2004/0181238 A1 | 9/2004 | Zarbatany et al. |
| 2005/0034735 A1 | 2/2005 | Deem et al. |
| 2006/0009800 A1 | 1/2006 | Christianson et al. |
| 2006/0106278 A1 | 5/2006 | Machold et al. |
| 2007/0049970 A1 | 3/2007 | Belef et al. |
| 2007/0185530 A1 | 8/2007 | Chin-Chen et al. |

FOREIGN PATENT DOCUMENTS

| | | |
|---|---|---|
| EP | 769272 | 4/1997 |
| EP | 861632 | 9/1998 |
| WO | WO 95/15715 | 6/1995 |
| WO | WO 95/25468 | 9/1995 |
| WO | WO 97/27807 | 8/1997 |
| WO | WO 97/27893 | 8/1997 |
| WO | WO 98/57585 | 12/1998 |
| WO | WO 99/00059 | 1/1999 |
| WO | WO 99/13777 | 3/1999 |
| WO | WO 99/15223 | 4/1999 |
| WO | WO 00/03759 | 2/2000 |
| WO | WO 00/59382 | 10/2000 |
| WO | WO 00/60995 | 10/2000 |
| WO | WO 01/26557 | 4/2001 |
| WO | WO 01/28432 | 4/2001 |
| WO | WO 01/66018 | 9/2001 |
| WO | WO 01/95809 | 12/2001 |
| WO | WO 02/24078 | 3/2002 |
| WO | WO 02/34167 | 5/2002 |
| WO | WO 03/001893 | 1/2003 |

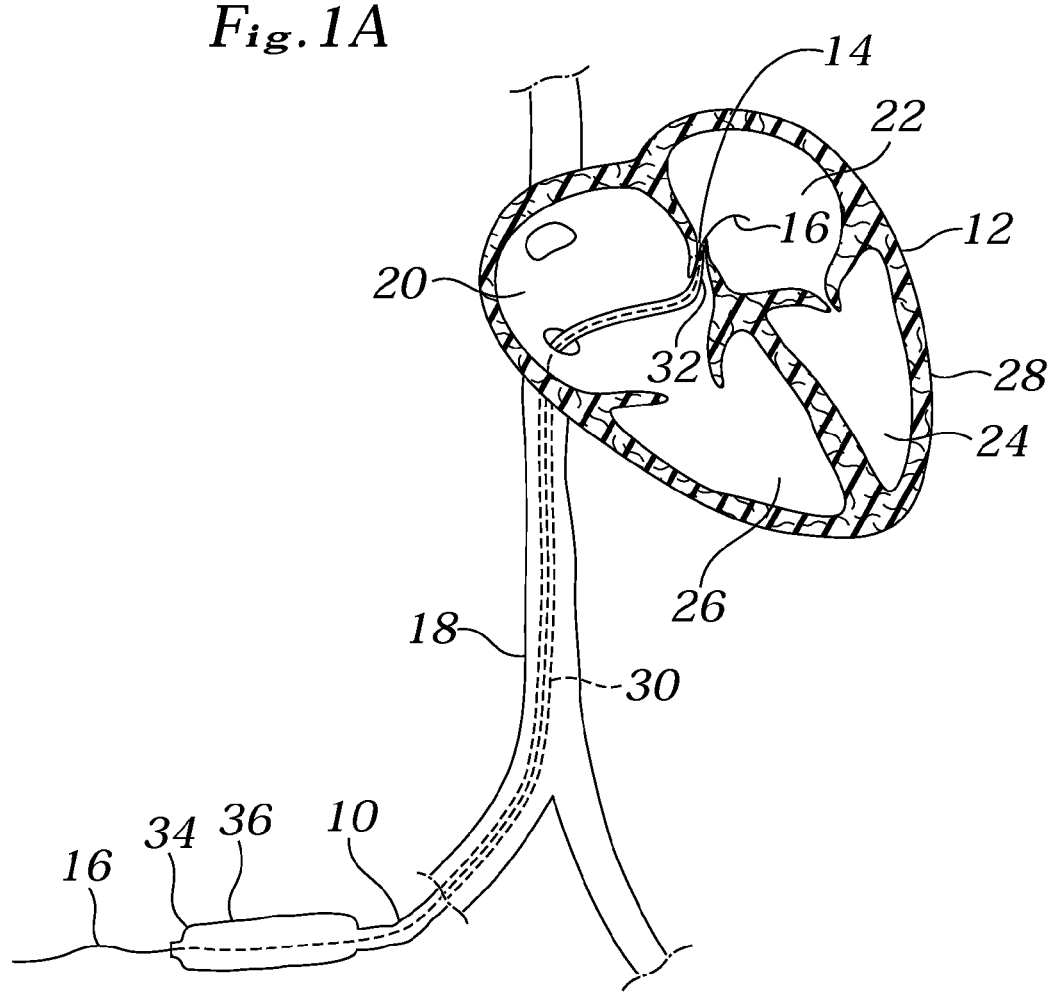

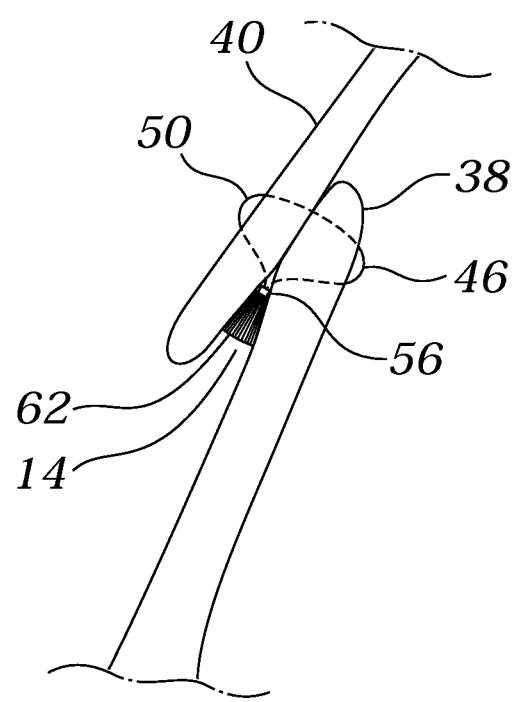

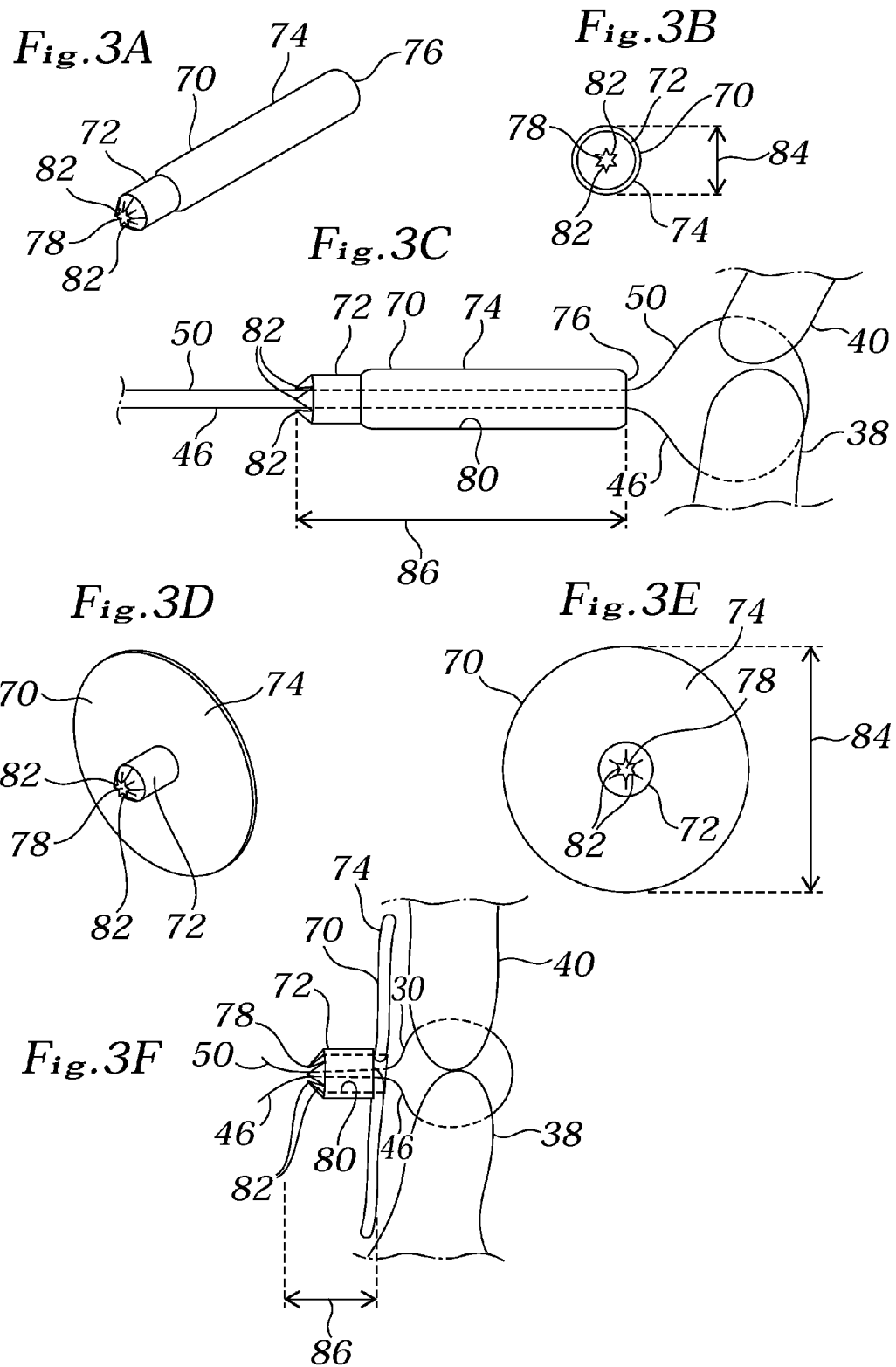

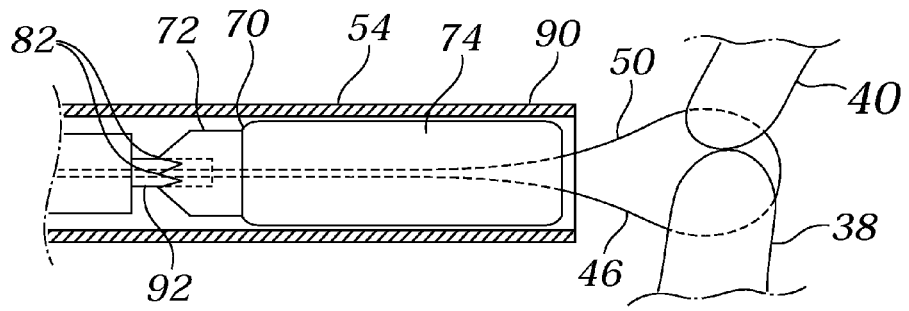
Fig.4A
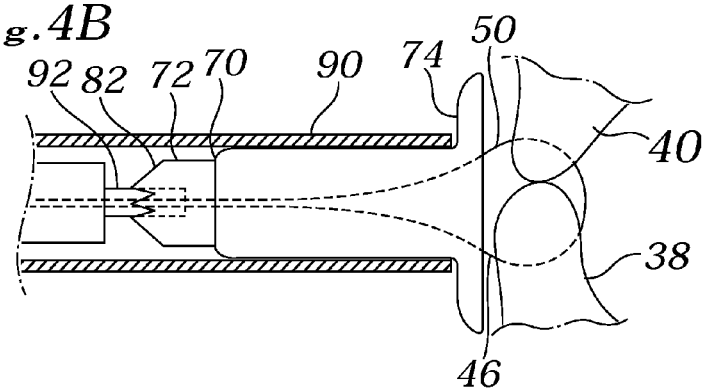
Fig.4B
Fig.4C
Fig.4D

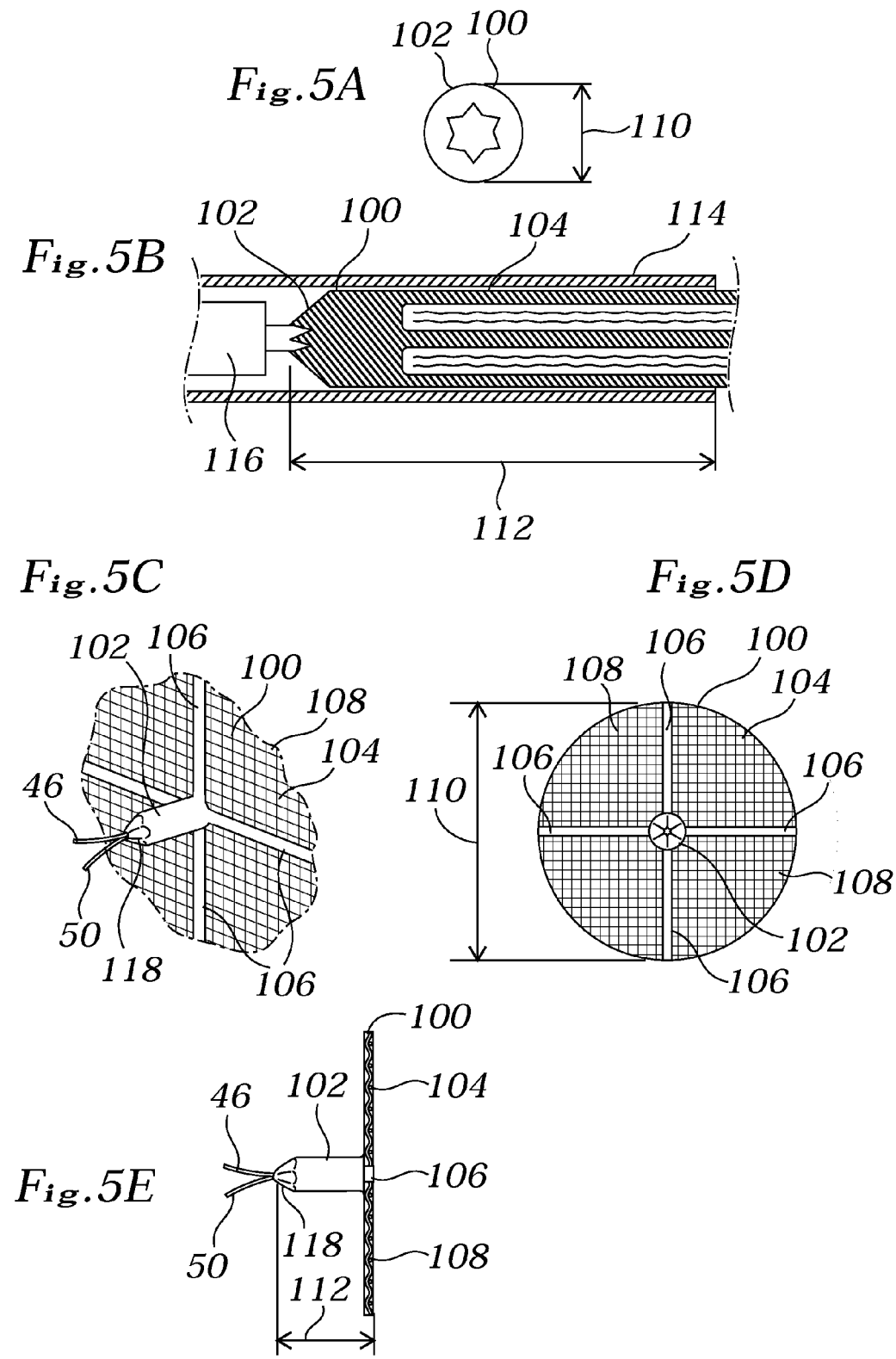

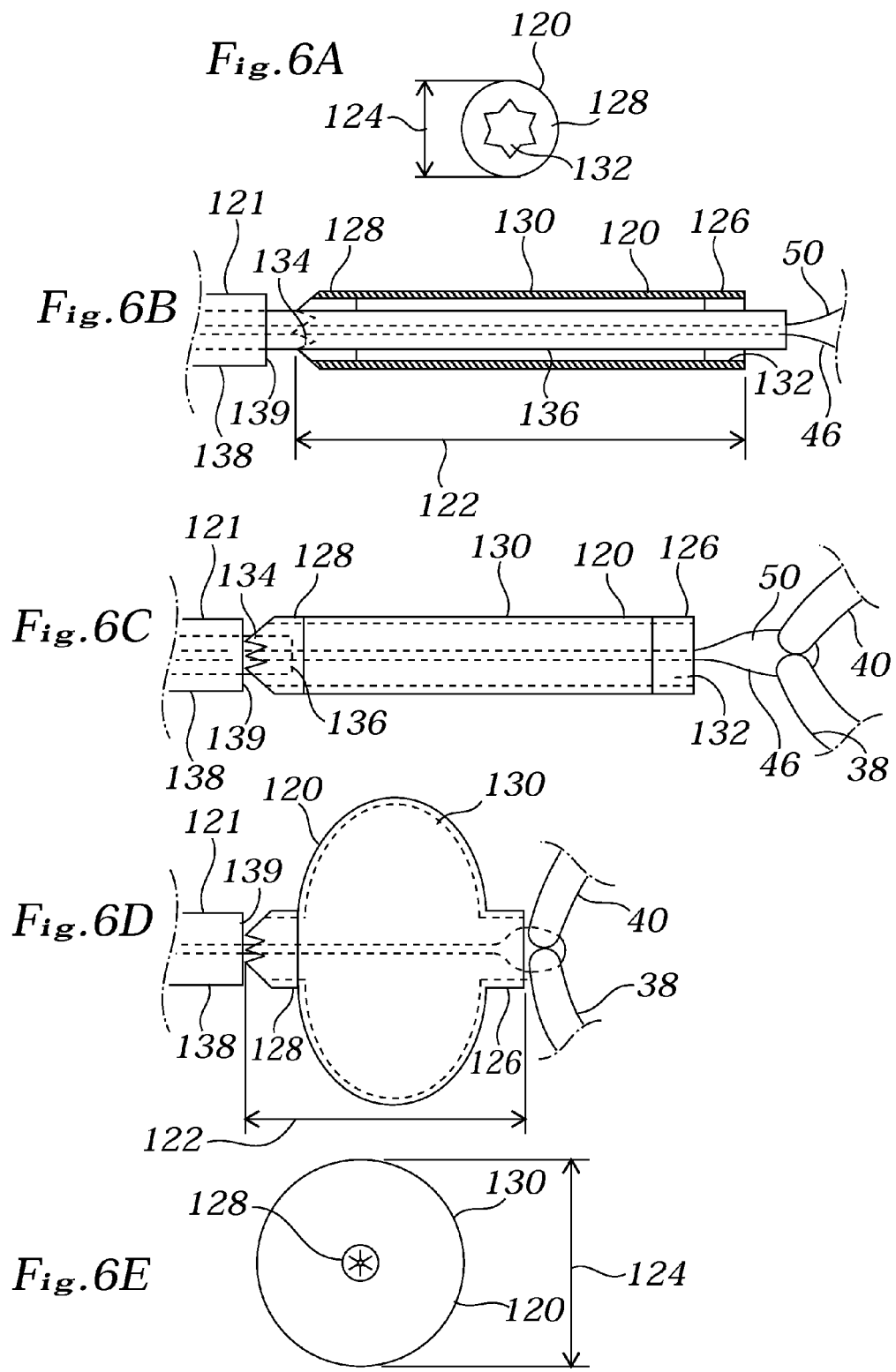

EXPANDABLE CLIP FOR TISSUE REPAIR

CROSS REFERENCE TO RELATED APPLICATIONS

The present application is a continuation of pending U.S. patent application Ser. No. 11/635,095 filed Dec. 7, 2006 now abandoned and entitled "Expandable Clip for Tissue Repair," which claims priority to U.S. Provisional Application No. 60/843,267, filed Sep. 8, 2006 and entitled "Expandable Clip for Tissue Repair," the entire contents of each of which are hereby incorporated herein by reference.

FIELD OF THE INVENTION

The present invention relates to medical devices and methods. In particular, the present invention relates to a system, apparatus, and method for repairing tissue, and particularly for repairing septal defects, such as a patent foramen ovale (PFO).

BACKGROUND OF THE INVENTION

Septal defects are a relatively common occurrence. While many septal defects are relatively benign and have little or no impact on a person's health, other septal defects can be more serious.

One type of septal defect is a patent foramen ovale (PFO), which is an opening between the right atrium and the left atrium. Because the fetal lungs do not provide air prior to birth, fetal blood is oxygenated by the mother via the umbilical cord and placentia. To provide for such circulation, the fetal blood circulation system includes several vessels and openings that remain open during fetal development but that close soon after birth. One such opening is the foramen ovale, which permits blood to flow from the right atrium into the left atrium in a fetal heart, thereby allowing blood to bypass the fetal lungs and flow directly from the venous circulation to the arterial circulation.

After birth, the infant's lungs typically provide oxygenation to the blood, and it is generally undesirable to continue having blood flow from the venous circulation to the arterial circulation without first passing through the lungs. Accordingly, it is generally desirable that the foramen ovale be closed after birth.

At birth, left atrial pressure increases as the pulmonary circulation is established. For most newborn infants, this pressure increase causes the closure of a flap of tissue which occludes the foramen ovale and then heals in the occluded position shortly after birth. In a significant percentage of persons, however, the tissue flap does not heal to permanently occlude the foreman ovale. This condition is known as a patent (i.e., open) foramen ovale (PFO).

While a PFO can be a relatively benign condition, PFOs have been associated with migraines. PFOs can also cause strokes by permitting blood containing small thrombi to bypass the lungs (which would otherwise filter out such small thrombi) and flow directly from the venous circulation to the arterial circulation and into the brain.

Treatments for PFOs range from open-heart surgery to percutaneous procedures. Open-heart surgery for PFOs typically involves suturing the PFO closed. Although relatively simple, such open-heart surgical treatment is associated with all the usual risks of cardiac surgery. Percutaneous methods include deploying mesh, clamshell, or other similar implanted devices to close the PFO. Other treatments include using heat, laser, RF, or other energy to treat the tissue of (or adjacent to) the PFO to induce the tissue to permanently close the PFO. Many of these percutaneous methods are often complicated and may involve relatively large implanted devices or uncertain tissue treatments.

One particularly effective method for repairing a PFO involves the percutaneous introduction of a catheter having a needle and suture assembly, with the suture percutaneously passed, via one or more needles deployed via the catheter, through the tissue surrounding the PFO. The catheter is withdrawn and the user tightens the suture to assess whether the suture has been deployed to properly close the PFO. The suture is then secured via tying or clipping, and the excess suture is cut and removed. The PFO is thus held closed by the tightened suture. Such a method and apparatus is disclosed in co-pending U.S. patent application Ser. No. 11/174,143, filed Jun. 30, 2005, the entire contents of which are expressly incorporated herein by reference. Other methods, systems, and devices for deploying suture that may be applicable for use with the current invention are disclosed in Applicant's U.S. Pat. Nos. 6,537,290; 6,626,930; 6,860,890; 6,719,767; 7,011,669; 7,083,628; and 7,094,244; and also in Applicant's co-pending U.S. application Ser. Nos. 10/233,879 and 10/389,721; the contents of each of which are incorporated in entirety herein by reference.

In light of the foregoing, there is presently a need for improved systems for treating PFOs. More specifically, there is a present need for an improved method, apparatus, and system for repairing PFOs. The current invention meets this need.

BRIEF SUMMARY OF THE INVENTION

Embodiments of the present invention provide devices and methods for effectively treating a tissue opening, such as a PFO or other septal defect, and particularly for effectively treating an opening that may be unsuitable for closure using suture alone. Preferred embodiments of the invention provide devices and methods wherein a PFO is treated via a catheter from a remote insertion location.

In one aspect, the present invention is a suture-securing fastener or clip, similar to earlier suture-securing clips used in percutaneous edge-to-edge heart valve leaflet repairs and PFO closures except that the current fastener is expandable upon delivery so that the clip itself serves to physically block the opening which the procedure is attempting to close. The clip serves as a closure and/or treatment device. The clip has a center suture-receiving lumen so that the clip can be advanced into the patient's body to the desired treatment site by being slid along one or more suture lines previously deployed, with the one or more suture lines passing from the desired treatment site to a position outside of the patient's body. The suture line thus acts, during clip delivery and deployment, as a guide for proper placement of the clip. Once the clip is at the desired treatment site (which is typically at or adjacent the opening to be closed) and the suture is tightened as desired, the clip locks onto the suture (via a locking clip portion) to hold the suture and clip securely in position. The clip is then expanded to its expanded configuration in order to physically block the opening that is being closed, so that the expandable portion of the clip serves as a plug portion. Alternatively, the expandable plug portion of the clip can be expanded prior to being locked into place on the suture, so that the user can check the positioning of the clip and the efficacy of the blockage created thereby, and the clip can then be locked securely onto the suture line to hold the clip and suture in the desired location and positioning. The expansion and locking of the clip can also occur as a single step, depending on the particular application and clip configuration. If the desired closure is not achieved, the expanded clip can be retrieved into its protective sheath (which can involve de-expanding the clip), the catheter removed, and the procedure aborted. The suture lines can then be removed and/or additional attempts can be made to perform the procedure, which may include using one or more different clips and/or different suture lines.

The expandable clip can expand mechanically once it is positioned at the desired treatment site. The expansion could be achieved by a generally umbrella-shaped structure, an inflatable structure, an expandable cage-like structure, and/or other configurations. The expandable clip could include an expandable sponge-like, foam-like, and/or adhesive-like material, which could expand from or around the clip. The expansion could be activated by the user, or be an inherent quality of the clip when exposed to the interior environment of the patient's body (e.g., an expandable sponge-like material that expands when exposed to blood and/or other body fluids). The expandable clip may include additional structures to hold the clip in place, such as tissue-penetrating spikes, etc. The clip may be configured to encourage tissue ingrowth onto or into the clip, which may include providing one or more tissue-growth-inducing material in the clip. In some applications, such as where a blockage is desired to be temporary, the clip may be configured to discourage tissue ingrowth so that the clip can be removed later. The clip may be configured to be reduced in diameter after it has been expanded to its deployed size, so that a user can reposition and/or remove the clip after it has been initially expanded within the patient's body.

In one aspect, the present invention is directed to a system and method for repairing a PFO with a treatment catheter capable of applying at least one suture to the tissue adjacent the PFO. The invention can further use a fastener catheter capable of attaching at least one fastener to the suture. In addition, the fastener catheter can include at least one cutting member configured to cut the suture to a desired length. The fastener of the invention can be configured so that it expands upon deployment, so that the bulk of the expanded fastener itself helps to close the septal defect.

In another aspect, the present invention includes a system and method for repairing a PFO using a fastener and patch combination. The fastener and patch can be deployed separately, e.g., by separate catheters, or together, e.g., by a single catheter. In one such embodiment, a system for repairing a PFO and includes a treatment catheter capable of applying at least one suture to the tissue adjacent the PFO, and a fastener catheter capable of attaching at least one fastener and a patch to the suture. The patch is positioned distally of the fastener, so that when the fastener is advanced into the patient, the patch is also advanced to the PFO site. With the patch and fastener advanced to the PFO, the user can determine the adequateness of the PFO closure, and deploy the fastener to hold the suture tight and also to hold the patch in place or, if the PFO closure is inadequate, the user can remove the patch, fastener, and/or suture lines and either abandon the repair attempt or retry using one or more different patches, fasteners, and/or suture lines. If the user completes the deployment of the fastener and patch, the patch will be positioned between the fastener clip and tissue through which the suture has passed, and the patch is thus held (by the fastener) against and/or within the PFO to effectuate the PFO closure.

In yet another aspect, the present invention discloses a system for repairing tissue within the heart of a patient and includes a guide wire capable of being inserted into the patient and advanced through a circulatory pathway, a treatment catheter attachable to the guide wire and capable of applying at least one suture to the tissue, and fastener catheter attachable to the guide wire and capable of attaching at least one fastener to the suture, and a fastener configured to expand upon deployment. A patch may also be included with a system and method. The patch may be used with the expandable fastener, or with a non-expandable fastener. The patch may be deployed with or separately from the fastener.

In another embodiment of the invention, tissue-irritating materials are used to speed the healing process whereby the tissue adjacent the PFO grows over the suture, fastener, and/or patch. The fastener may include tissue-irritating materials in its structure, including tissue-irritating materials in the expandable portion of the fastener. The patch may also include tissue-irritating materials, such as tissue-irritating cloth. In a further embodiment, the suture has enhanced tissue-irritating characteristics.

The present invention also discloses various methods of treating a PFO within the body of a patient. In one aspect, a method of treating a PFO is disclosed which includes advancing a guide catheter through a circulatory pathway to a location in the heart proximate to a PFO, advancing a PFO treatment catheter through the guide catheter to the PFO, deploying a first suture into the stabilized first adjacent tissue portion, deploying a second suture into the second adjacent tissue portion, reducing the distance between the first and second sutures, advancing an expandable clip along the first and second sutures to the PFO, expanding the expandable clip adjacent or within the PFO, assessing the efficacy of the PFO repair, and deploying the expandable clip adjacent or within the PFO. The method may also include stabilizing the first and second adjacent tissue portions, which may be performed by applying a vacuum. The vacuum may first be applied to stabilizing a first adjacent tissue portion with the treatment catheter, then removed to release the first adjacent tissue portion, followed by application of the vacuum to stabilize the second tissue portion, then removed to release the second adjacent tissue portion.

An alternate method of treating a PFO is disclosed and comprises advancing a guide catheter through a circulatory pathway to a location in the heart proximate the PFO, advancing a PFO treatment catheter through the guide catheter to the PFO, deploying a first suture into the stabilized first adjacent tissue portion, deploying a second suture into the second adjacent tissue portion, advancing a patch over the first and second sutures to a position adjacent or within the PFO, advancing a fastener over the first and second suture to a position adjacent or within the PFO, tightening the first and second sutures, assessing the efficacy of the PFO closure, and deploying the fastener. The method may also include expanding the fastener adjacent to or within the PFO.

Other objects, features, and advantages of the present invention will become apparent from a consideration of the following detailed description.

BRIEF DESCRIPTION OF THE DRAWINGS

FIG. 1A illustrates a suture-deploying treatment catheter advanced within a patient's vasculature and into a PFO according to an embodiment of the invention;

FIG. 2D depicts the a close-up side view of the PFO, with the excess suture cut from the first and second sutures;

FIGS. 3A, 3B, and 3C depict perspective, end, and side (with partial cross section) views, respectively, of a fastener in the unexpanded condition according to an embodiment of the invention;

FIGS. 3D, 3E, and 3F depict perspective, end, and side (with partial cross section) views, respectively, of the fastener from FIGS. 3A, 3B, and 3C in the expanded condition according to an embodiment of the invention;

FIGS. 4A through 4D depict side views of a fastener being deployed from a catheter according to an embodiment of the invention;

FIGS. 5A and 5B depict end and side (with partial cross section) views, respectively, of a fastener in the unexpanded condition according to an embodiment of the invention;

FIGS. 5C, 5D, and 5E depict perspective, end, and side (with partial cross section) views, respectively, of a fastener from FIGS. 5A and 5B in the expanded condition according to an embodiment of the invention;

FIGS. 6A and 6B depict end and side (with partial cross section) views, respectively, of a fastener in the expanded condition according to an embodiment of the invention;

FIG. 6C depicts a side view, in cross section, of the fastener of FIGS. 6A and 6B being deployed from a catheter according to an embodiment of the invention;

FIGS. 6D and 6E depict end and side (with partial cross section) views, respectively, of the fastener from FIGS. 6A and 6B in the expanded condition according to an embodiment of the invention;

DETAILED DESCRIPTION OF THE INVENTION

Figure 1B:
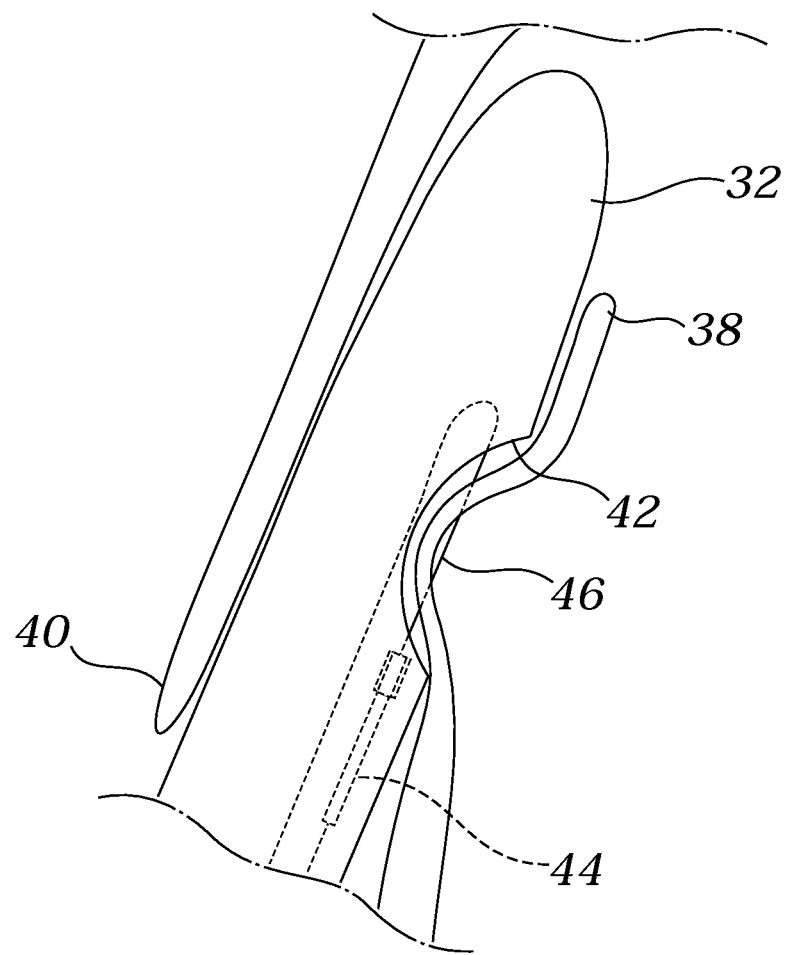
FIG. 1B illustrates a close-up of the suture-deploying treatment catheter of FIG. 1B deploying a first suture through a first tissue portion adjacent the PFO according to an embodiment of the invention.

The invention is an apparatus, system, and method for treating a patent foramen ovale (PFO) to cause closure thereof. More specifically, the invention provides for percutaneous or other minimally-invasive application of suture to PFO to cause closure of the PFO.

FIG. 1A depicts a suture-deploying treatment catheter 10 according to the invention being advanced through a patient's vasculature to a heart 12 and into a PFO 14. A guidewire 16 has previously been advanced through the vasculature by passing up the inferior vena cava 18, through the right atrium 20, and through the PFO 14 and into the left atrium 22. Note that other introductory routes, including other percutaneous and minimally invasive routes, are also within the scope of the invention. For example, the guidewire and device could be introduced through heart vessels leading to the left ventricle 24 or right ventricle 26, and then on to access the PFO 14 through either the right atrium 20 or left atrium 22. Depending on the particular embodiment, the device may also be introduced through the heart wall 28, as may be the case in a minimally-invasive surgical procedure conducted through a patient's chest cavity. The particular route selected for introduction of the device to the PFO 14 depends on various factors, including the condition of the patient. While the embodiment of FIG. 1A includes a guidewire 16 to guide the treatment catheter 10 into position, the guidewire 16 does not have to be present in all embodiments, such as where the treatment catheter 10 is steerable on its own to the PFO 14.

The treatment catheter 10 comprises a generally elongated body 30 having a distal end 32 and a proximal end 34. A handle 36 is located at the proximal end 34. The treatment catheter 10 has sufficient length to reach the PFO 14 from outside the patient's body via the particular route selected. For a percutaneous route, the treatment catheter will generally have a length on the order of 60 to 90 cm. Other access routes may require different lengths. The elongated body 30 and distal end 32 have a diameter that is small enough to pass through the particular blood vessels and/or openings of the particular access route selected. While percutaneous approaches through the inferior vena cava, as depicted in FIG. 1, can accommodate diameters of 12 to 16 Fr for the treatment catheter when used with an introducer sheath (which may have a diameter of 16 to 21 Fr depending on the particular application), other approaches and/or omitting the introducer sheath may permit and/or require delivery catheters having smaller or larger diameters.

The PFO is often a generally tunnel-shaped opening. In the embodiment depicted, the treatment catheter distal end 32 is positioned within the tunnel-like PFO. FIG. 1B depicts a close-up view of the catheter distal end 32 positioned within the tunnel-like PFO, between first and second tissue portions 38, 40, which in the particular embodiment depicted are a septum primum and septum secundum, respectively. Note that in most persons the septum primum will have healed permanently to the septum secundum, thereby permanently closing the foramen ovale. In a patient having a PFO, however, the septum primum will not have healed in the closed position, and instead acts a flap that only partially occludes blood flow between the right and left atria.

In the embodiment of FIG. 1B, a vacuum recess 42 at the catheter distal end 32 is generally crescent- or wedge-shaped in profile. The vacuum recess 42 has been positioned adjacent the first tissue portion 38, which has been drawn via the application of vacuum into the vacuum recess 42. A first needle 44 attached to a first suture line 46 is retracted proximally across the vacuum recess 42 to pass through the first tissue portion 38, so that the first suture line 46 is drawn through the first tissue portion 38.

Once the first needle 44 has been passed through the first tissue portion 38, the first needle 44 is further retracted so that it is entirely clear of the first tissue portion 38 and only the first suture line 46 passes therethrough. The vacuum can then be discontinued, so that the first tissue portion 38 is released from the vacuum recess 42. The catheter distal end 42 and vacuum recess 42 can then be moved respectively away from the first tissue portion 38 and toward the second tissue portion 40, with the first suture line 46 playing out from the catheter distal end 32.

Figure 1C:
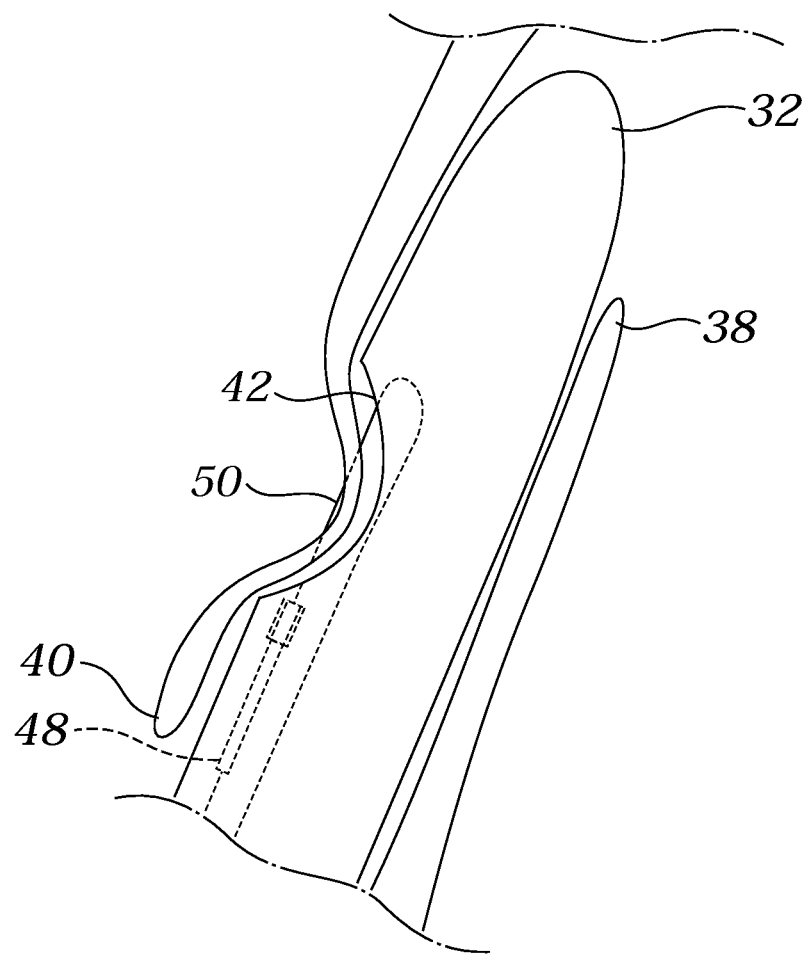
FIG. 1C illustrates a close-up of the suture-deploying treatment catheter of FIG. 1B deploying a second suture through a second tissue portion adjacent the PFO according to an embodiment of the invention.

FIG. 1C depicts the catheter distal end 32 repositioned with the vacuum recess 42 adjacent the second tissue portion 40, which in the particular embodiment depicted involved rotating the catheter distal end 32 by about 180 degrees. The second tissue portion 40 has been drawn via the application of vacuum into the vacuum recess 42. A second needle 48 attached to a second suture line 50 has been passed through the second tissue portion 40, drawing the second suture line 50 through the second tissue portion.

Figure 1D:
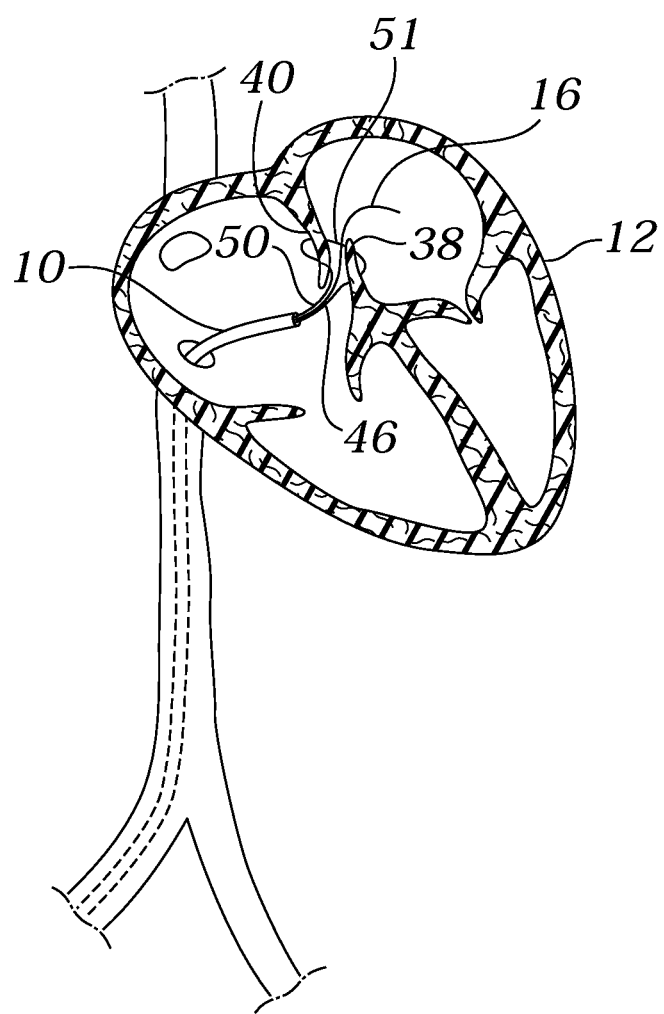
FIG. 1D illustrates the suture-deploying treatment catheter being withdrawn from the patient's vasculature, trailing the first and second suture lines behind according to an embodiment of the invention.

Once the second needle 48 has been passed through the second tissue portion 40, the second needle 48 is further retracted so that it is entirely clear of the second tissue portion 40 and only the second suture line 50 passes therethrough. The vacuum can then be discontinued, so that the second tissue portion 40 is released from the vacuum recess 42. The treatment catheter 10 can then be withdrawn from the patient, as depicted in FIG. 1D. As the treatment catheter 10 is withdrawn, the suture lines 46, 50 play out from the treatment catheter 10. In the particular embodiment depicted, the suture lines 46, 50 meet at their distal ends and connect to form one continuous length of suture 51.

FIGS. 1A-1D depict a treatment catheter having a single vacuum port, two needles, and two lines of suture forming a single common suture. However, other treatment catheters, needle assemblies, and suture assemblies are also within the scope of the invention. For example, a catheter having two or more vacuum ports (or other tissue-stabilizing devices), with one or more needles and sutures with each vacuum port, could be used. Such a catheter could simultaneously grasp and/or suture both the first and the second tissue portions. A treatment catheter having only a single needle and suture could also be used with the invention, as could any treatment catheter capable of delivering at least one line of suture percutaneously through at least one tissue portion adjacent the PFO (or other opening to be closed).

Note that it may be desirable in some applications that the first and/or second tissue portions for suturing be selected from well within the tunnel-like PFO, and/or within a distal (from the user's viewpoint) portion of the tunnel-like PFO or other opening to be treated. This will result in the suture lines passing through tissue well within the PFO, so that any fastener subsequently deployed on proximal portions of the suture lines can be deployed well within the tunnel-like PFO. The selection of tissue for suturing, however, depends on numerous factors, including the particular PFO or other structure being occluded or treated, the condition of the surrounding tissue, the particular fastener being deployed, the likes and/or dislikes of a particular user, etc.

FIGS. 1A-1D depict two suture lines (which together form one continuous suture line) being deployed through tissue at the treatment site. However, other numbers of suture lines are also within the scope of the invention. For example, multiple sutures could be deployed in and/or around a treatment site to enhance the closure of the final suture/fastener combination.

Figure 2A:
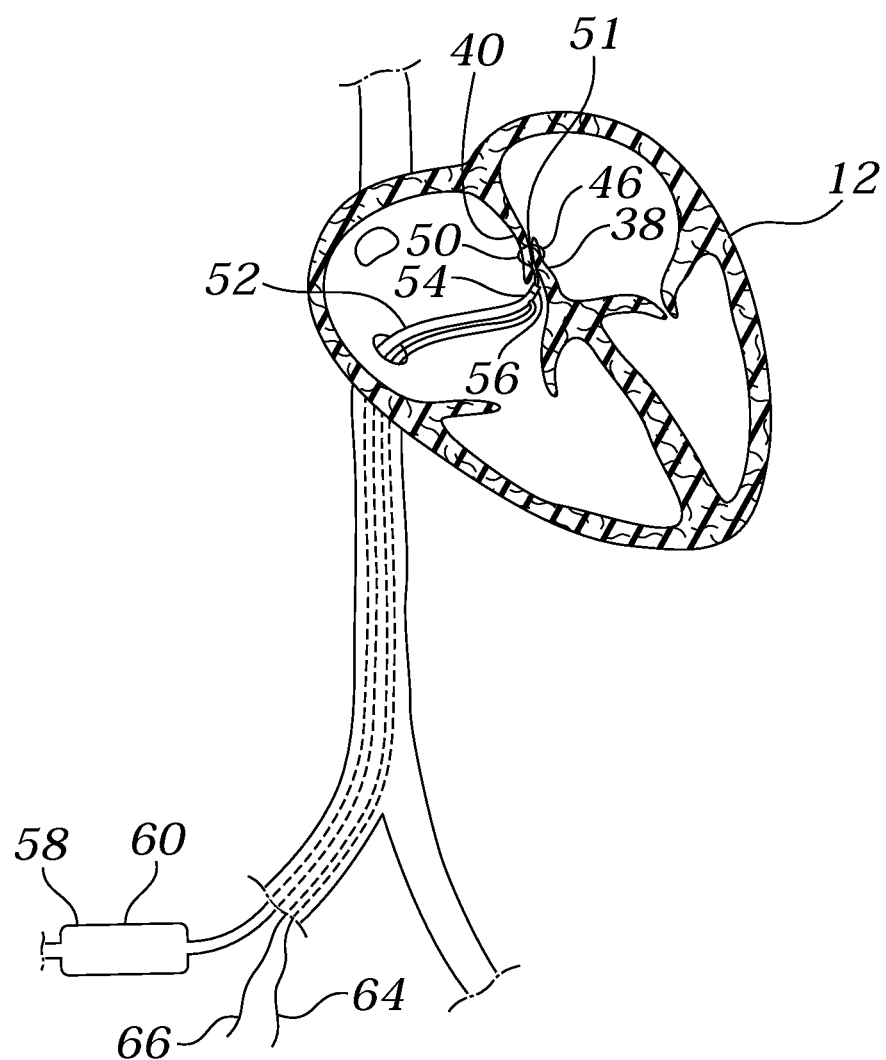
FIG. 2A illustrates a fastener-deploying catheter being advanced within a patient's vasculature over the first and second suture lines and into the PFO according to an embodiment of the invention.

FIG. 2A depicts a fastener catheter 52 being advanced over the suture lines 46, 50 within the patient's vasculature toward the patient's heart 12 and the PFO 14. (Note that the guide wire has been removed, with the suture lines 46, 50 now serving the catheter guiding purpose formerly performed by the guide wire. Alternatively, the guide wire could remain in place.) The fastener catheter 52 includes a distal end 54 having a fastener 56 mounted thereon, and a proximal end 58 having a handle 60. Trailing portions 64, 66 of the suture lines 46, 50 pass outside of the fastener catheter 52 through an opening therein just proximally of the fastener catheter distal end 54 and then pass through the patient's vasculature and outside of the patient. Note that trailing suture portions could alternatively pass through the length of a fastener catheter and exit out the proximal end thereof in a manner similar to the way a guide wire passes through so-called "over-the-wire" delivery catheters.

Figure 2B:
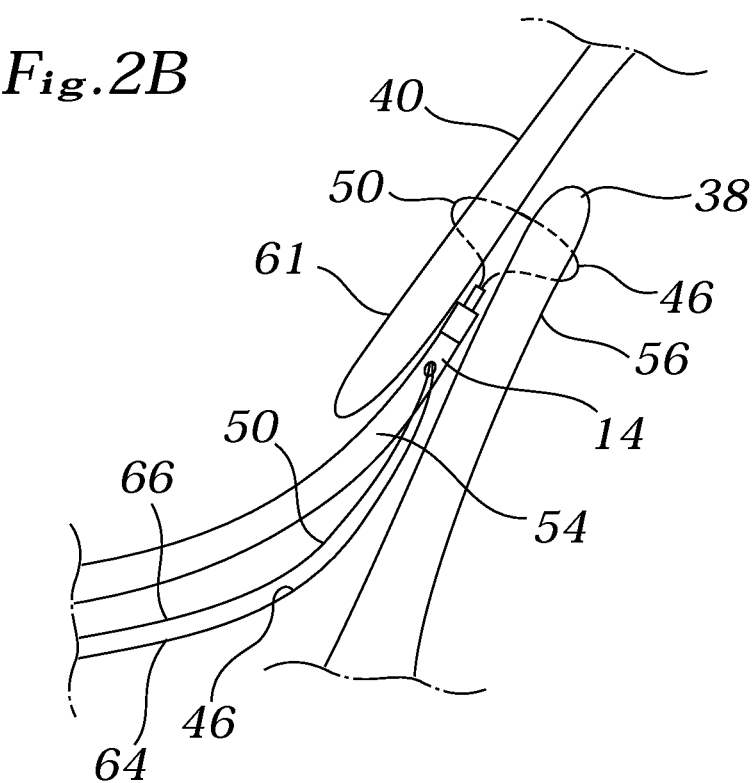
FIG. 2B depicts a close-up side view of the fastener-deploying catheter advanced within the PFO, with the fastener positioned within the PFO.

In FIG. 2B, the fastener catheter distal end 54 and fastener 56 have been advanced into the PFO 14, with the suture lines 46, 50 (which trail out of the opening 61 in the fastener catheter distal end 54) tightened to draw the tissue portions 38, 40 together. With the tissue portions 38, 40 drawn together, the user can confirm the efficacy of the suture lines placement and/or PFO closure, which can be accomplished via fluoroscopy, echo, or other visualization and/or assessment techniques. If the user determines that the results are not satisfactory, the procedure can be aborted by removing the fastener catheter 52 (including the fastener 56) from the patient's body and also removing the suture lines 46, 50, which in the embodiment depicted can be achieved by pulling on one of the trailing portions 64, 66 while letting go of the opposing trailing portion, thereby removing the continuous suture loop formed by the suture lines 46, 50.

Figure 2C:
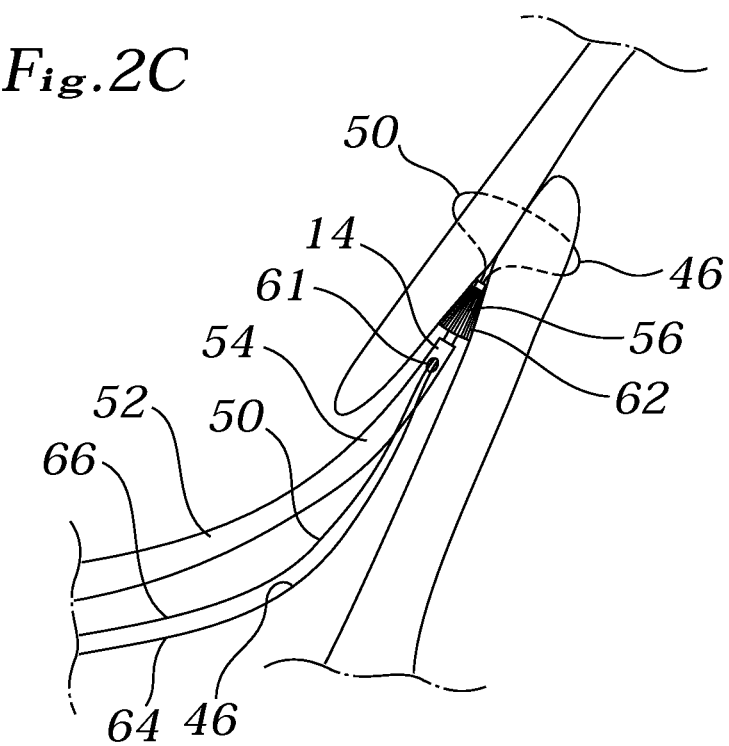
FIG. 2C depicts a close-up side view of the fastener-deploying catheter advanced within the PFO, with the fastener expanded and deployed to secure the first and second suture lines within the PFO.

In FIG. 2C, the fastener 56 is expanded and deployed, so that the fastener 56 is released from the fastener catheter 52 and securely holds the suture lines 46, 50 in place. The fastener 56 is also expanded, with the expandable portion 62 blocking the PFO 14. Note that the expansion and deployment of the fastener can be performed as a single step, or as separate steps, depending on the particular fastener and other parameters. If the expansion and deployment are performed separately, the expansion may be performed first, or the deployment may be performed first, again depending on the particular fastener and other parameters. With the fastener 56 deployed, the catheter distal end 54 can be retracted over the suture lines 46, 50 from the patient.

In FIG. 2D, the fastener catheter has been removed from the PFO 14, and the trailing suture portions have been cut from the suture lines 46, 50 (i.e., the suture lines 46, 40 have been cut short adjacent the fastener 56). Depending on the particular application and catheters involved, the excess suture portions can be cut by the fastener catheter itself if the fastener catheter is configured to cut suture. The excess suture portions could alternatively be cut by a separate catheter configured to cut suture. Examples of catheters having integrated suture cutting mechanisms are disclosed in pending U.S. patent application Ser. Nos. 11/174,143 and 11/174,357, the contents of each of which are incorporated herein in their entirety by reference. The expanded portion 62 of the expanded fastener 56 serves to occlude the PFO 14 and/or (depending on the particular fastener) serves as a structure over which tissue can form to occlude the PFO 14.

In the embodiment depicted in FIGS. 1A-1D and 2A-2D, the treatment catheter and fastener catheters were advanced and positioned using a guide wire and/or the suture lines, but without a guide catheter. Depending on the particular application, however, including such factors as the flexibility or steerability of the treatment and/or fastener catheters, a guide catheter may be used with or without a guide wire, although most typically in combination with the guide wire. The guide catheter can be advanced over the guidewire to a position adjacent or within the PFO. The treatment and fastener catheters can then be advanced and withdrawn through the guide catheter.

Various fastener designs and configurations are within the scope of the invention. Examples of some fasteners are discussed below.

FIGS. 3A-3F depict an expandable fastener 70. In the side views of FIGS. 3C and 3F, the fastener 70 is depicted positioned over first and second suture lines 46, 50 and advanced adjacent first and second tissue portions 38, 40 according to an embodiment of the invention. The expandable fastener 70 is depicted in FIGS. 3A-3C in its unexpanded configuration, and in FIGS. 3D-3F in the expanded condition. The expandable fastener 70 includes a locking clip portion 72 and an expandable plug portion 74. In the particular embodiment depicted, the locking clip portion 72 has a distal opening 76, a proximal opening 78, and a central suture lumen 80 running between the two openings 76, 78. The locking clip portion 72 includes a lock in the form of a plurality of inwardly-directed teeth 82 that act to close off the clip proximal opening 78 when released. Note that in the unexpanded delivery configuration of FIGS. 3A-3C the teeth 82 are positioned in an "open" configuration, so that the proximal opening 78 and central suture lumen 80 are largely unobstructed, and the suture lines 46, 50 can pass freely therethrough. In the deployed configuration of FIGS. 3D-F, however, the teeth 82 are in their "closed" position, where they are directed inward and obstruct the proximal opening 78, thereby preventing movement of the suture lines 46, 50 through the fastener 70. The locking clip portion 72 can be formed from a memory material such as Nitinol, and the teeth 82 may be biased toward the "closed" position. The locking clip portion 72 is preferably dimensioned to accommodate one or more suture lines therethrough, such as the two suture lines 46, 50 depicted. The dimensions of the locking clip portion 72 depend on the particular application, but a relatively small outer diameter is generally desirable for percutaneous applications. In one example of a locking clip, the locking clip has an outer diameter of about 0.080 inches, a suture lumen inner diameter of about 0.050 inches, and a length of about 0.060 inches. Note that other dimensions are also within the scope of the invention, with the selection of specific dimensions being dependant on a particular application.

The fastener 70 also includes an expandable plug portion 74, which in the particular embodiment of FIGS. 3A-3F is a generally flat disk of a flexible material that can be placed in an unexpanded configuration where it is tightly positioned to give the fastener 70 a relatively small diameter 84 as depicted in FIGS. 3A-3C, but can expand to a much larger diameter 84 as depicted in FIGS. 3D-3F. As the fastener 70 expands in diameter, the length of the expandable plug portion 74 shortens, thereby causing a corresponding shortening in the length 86 of the fastener 70. The expandable plug portion 74 may be formed from various materials, including biocompatible materials, bioresorbable materials, and/or tissue-growth inducing materials. For example, the expandable plug portion could be formed from a biocompatible polymer that can flex but will re-expand after being compressed or otherwise deformed. The expandable plug portion 74 and/or locking clip portion 72 may be formed and/or coated with materials that promote tissue ingrowth, such as tissue-irritating materials that can provoke a tissue growing response from the surrounding tissue. The expandable plug portion 74 may be biased toward its expanded shape, so that it must be physically held in the desired delivery shape (with smaller diameter) but will expand to the desired expanded shape (and larger diameter) when released. The expanded and delivery dimensions of the fastener and expandable plug portion depend on the particular application. It may generally be desirable to have a minimal unexpanded diameter for the expandable plug portion in order to facilitate percutaneous delivery of the fastener. The expandable plug portion may have an unexpanded (delivery) diameter that is about the same as that of the locking clip portion. For example, the expandable plug portion may have an unexpanded diameter of about 0.080 inches. The expanded diameter of the expandable plug portion (and hence of the fastener) can vary depending on the particular application. For example, for relatively small PFO's a relatively small expanded diameter may be sufficient, while larger PFO's may require larger expanded diameters. Expanded diameters could range from 5 to 25 mm, and an expanded diameter of about 10 mm may be particularly useful in some applications.

The fastener 70 can be made of a single material or of a combination of materials. For example, the locking clip portion 72 could be formed from shape memory metal such as Nitinol, and combined with an expandable plug portion 74 formed from Nitinol, stainless steel, polymeric materials, other biocompatible materials, tissue-growth-inducing materials (e.g., Dacron), and/or various combinations thereof.

FIGS. 4A-4D depict a fastener 70 such as that depicted in FIGS. 3A-3F being deployed from a fastener catheter 52. In FIG. 4A, the fastener 70 is secured in a fastener-holding sheath 90 at the distal end 54 of the fastener catheter 52. A fastener catheter inner member 92 passes into the fastener proximal opening 78. The teeth 82 engage against the fastener catheter inner member 92, so that the inner member 92 serves to hold the teeth 82 in their "open" position while the inwardly-engaging teeth 82 secure the fastener 70 to the inner member 92. The sheath 90 physically holds the fastener expandable plug portion 74 in its delivery shape and diameter, and also may protect the fastener and the patient's tissues during delivery. The assembly is advanced over suture lines 46, 50 to tissue portions 38, 40, with the suture lines 46, 50 tightened.

In FIG. 4B, the sheath 90 is partially retracted from around the expandable plug portion 74, so that the expandable plug portion 74 begins to expand outwardly. As the sheath is retracted, the entire assembly may be advanced distally to maintain the sutures 46, 50 in the tightened condition and to maintain the fastener 70 adjacent the tissue portions 38, 40. In FIG. 4C, the sheath 90 is fully retracted from the fastener 70, and the expandable plug portion 74 is fully expanded. The fastener catheter inner member 92 is beginning to be slidingly retracted within the fastener catheter main body member 94, so that the leading edge 96 of the main body member 94 is engaging against the fastener clip portion 74 to push the fastener 70 off of the inner member 92. At this point in the procedure, the user can securely hold the fully expanded fastener 70 against the tissue portions 38, 40 and assess the quality of the PFO closure using methods such as fluoroscopy, echo, etc. If the user is not satisfied with the closure achieved with the fastener 70, the user can remove the fastener 70 entirely from the patient's body and then advance another fastener (possibly having a different size or other characteristics) to the site and/or abort the repair and instead use another PFO repair procedure. To remove the expanded fastener 70, the user advances the sheath 90 back over the fastener 70 to re-compress the fastener 70 to its unexpanded configuration, then withdraws the delivery catheter 52 and fastener 70 entirely from the patient. The user can then select another fastener, which may have a different diameter or other characteristics, and deliver the other fastener along the suture lines to the treatment site. The user can then assess the PFO closure achieved with the second fastener, and either deploy the second fastener or remove the second fastener in favor of a third, etc.

If the user is satisfied with the placement and expansion of the fastener 70, the user can release the fastener 70 from the delivery catheter 52 to lock the fastener 70 in position. In FIG. 4D, the fastener 70 has been pushed entirely off of the inner member 92, and the teeth 82 of the locking clip 72 now engage against the suture lines 46, 50 to hold the fastener securely against the tissue portions 38, 40.

FIGS. 5A-5E depict a further embodiment of a fastener 100 with a locking clip portion 102 and an expandable portion 104. The expandable portion 104 is formed from a plurality of struts 106, which could be formed from various materials, such as Nitinol wire that may be rounded to reduce stresses in strut bends. A flexible membrane 108 could be added to extend between the struts 106, with the struts 106 serving as scaffolding for the flexible membrane 108. The flexible membrane 108 could be formed of various materials, including biocompatible materials such as Dacron and/or PTFE. The flexible membrane 108 could be formed in various ways. For example, the flexible membrane 108 could be formed from two pieces of flexible material die cut in a generally circular shape (with a cutout at the center to accommodate the locking clip portion) to a desired diameter, with the first piece applied to one side of the struts and the second piece applied to the opposite side of the struts. The material(s) forming the flexible membrane 108 could be attached to the fastener 100 using various methods, including adhesives, sutures, etc. The flexible membrane 108, and/or the struts 106 and/or the locking clip portion 102, could include materials having tissue-growth-inducing properties to encourage the ingrowth of tissue over the expandable portion 174 and/or the locking clip portion 172.

In the delivery configuration depicted in FIGS. 5A-5B, the diameter 110 of the fastener 100 is relatively small but the length 112 is relatively large, with the struts 106 generally aligned longitudinally with the fastener clip portion 102 and suture lines 46, 50. In the side view of FIG. 5B, the fastener 100 is depicted lying within a constraining outer sheath 114 of a fastener delivery catheter 116.

In the deployed configuration depicted in FIGS. 5C-5E, the diameter 110 of the fastener 100 is much larger, with the struts 106 extending radially outward from the fastener clip portion 102 and with the flexible membrane 108 filling the gaps between the struts 106. The fastener 100 when expanded thus assumes a generally disk-like shape having a relatively small length 112. Note that the fastener depicted in FIGS. 5A-5E could be made using only the struts for the expandable portion, i.e., without the flexible membrane. FIGS. 5C and 5E depict the suture lines 46, 50, held between the teeth 118 of the locking clip portion 102.

FIGS. 6A-6E depict a further embodiment of an expandable fastener 120, with FIGS. 6A-6C depicting the unexpanded configuration (with FIGS. 6B and 6C depicting the fastener 120 on a fastener delivery catheter 121) and FIGS. 6D-6E depicting the expanded condition. The expandable fastener 120 has a length 122 and an outer diameter 124. The particular expandable fastener 120 includes a distal section 126, a proximal section 128, and a middle section 130 which, in the embodiment depicted, is an expandable section. The fastener 120 includes a suture lumen 132 passing through each of the three sections 126, 128, 130, which in the embodiment depicted in FIGS. 6B and 6C is also configured to receive an inner member 136 of the delivery catheter 121. The expandable middle section 130 may be formed from a generally flexible biocompatible material, such as polymers and/or flexible bioabsorbable materials, which will deform when subjected to longitudinal compression. In the particular embodiment depicted, the expandable middle section 130 is formed from a tubular section of a relatively thin and flexible membrane. The middle section 130 can be of various lengths and/or stiffness for different PFO sizes and shapes.

In the unexpanded delivery configuration depicted in FIGS. 6A-6B, the suture lumen 132 is generally unobstructed throughout the length 122 of the expandable fastener 120. As seen in FIG. 6B, the fastener 128 is mounted on an inner member 136 of the fastener delivery catheter 121, with multiple teeth 134 engaging against the catheter inner member 136 to hold the fastener 120 thereon. Note that the fastener 120 may not be self-expanding, so that an outer sheath on the fastener delivery catheter 121 may not be needed to constrain the fastener 120 during delivery.

To deploy the fastener 120, the catheter inner member 136 is retracted into the catheter main body 138, so that the leading edge 139 of the catheter main body 138 engages against the fastener proximal section 128 to push the fastener 120 off of the catheter inner member 136. Once the catheter inner member 136 is removed from all of the fastener 120 except for the fastener proximal section 128, as depicted in FIG. 6C, the user can expand the fastener 120 while still keeping the fastener 120 secured to the catheter 121, which includes maintaining the locking teeth 134 in the "open" position so that the suture lines 46, 50 can pass freely therethrough.

The expansion of the expandable middle section 130 can be achieved by pressing longitudinally (e.g., via a catheter), in a distal direction, against the fastener proximal section 128. Because the distal section 126 cannot substantially advance distally due to the resistance from the tissue portions 38, 40 and suture lines 46, 50, the expandable middle section 130 will be compressed between the distal section 126 and proximal section 128. As the expandable middle section 130 expands, the middle section length 131 is reduced (which also reduces the overall length of the entire fastener 122) while the outer diameter 124 is increased. When the expandable fastener 120 is expanded, as depicted in FIGS. 6D-6E, the expandable middle section 130 deforms to expand radially and shorten longitudinally.

Once the expandable middle section 130 reaches its fully expanded diameter, the proximal section 128 can be locked in place on the suture lines 46, 50, which can be accomplished in the embodiment depicted by freeing the teeth 134 (e.g., by removing the catheter inner member from within the teeth) to allow the teeth to at least partially obstruct the suture lumen 132 as it passes through the proximal section 128. The teeth 134 thus serve as a lock to hold the suture lines 46, 50 tightly between the tissue 38, 40 and fastener 120 while also holding the fastener 120 in its expanded condition. Note that other locks are also within the scope of the invention, including locks that prevent movement of the suture lines 46, 50 in just one direction (i.e., proximally through the suture lumen 132, or distally through the suture lumen 132) as well as locks that prevent movement of the suture lines 46, 50 in both the proximal and distal directions.

Figure 7A:
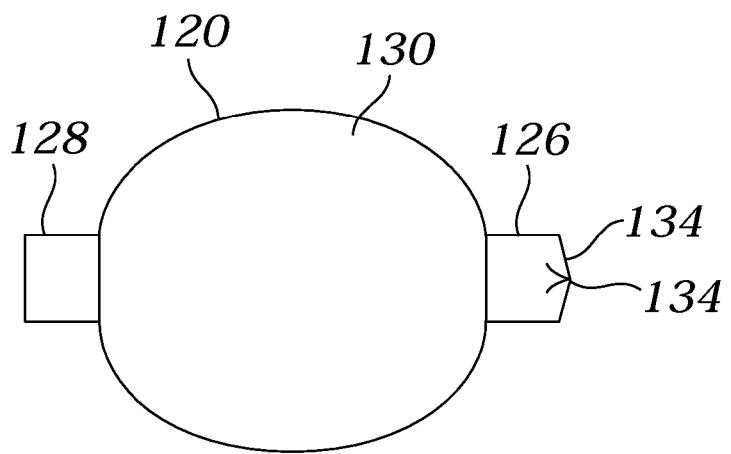
FIG. 7A depicts a side view in cross section of a fastener according to an embodiment of the invention.

In the embodiments of FIGS. 6A-6E, the suture lock in the form of the inwardly-projecting teeth 134 was positioned proximally of the expandable portion, namely in the fastener proximal section 128. In FIG. 7A, however, the lock in the form of teeth 134 is instead positioned in the distal section 126 of the fastener 120, with no locking mechanism being present in the proximal section 128 of the fastener 120. Such a configuration can be used with an expandable fastener wherein the expandable portion does not need a proximal locking portion to resist proximal deformation of the expandable portion after deployment and expansion. For example, where the expandable portion is permanently (i.e., non-elastically) deformed during expansion, or is locked into the expanded position by a locking mechanism other than a proximal-section lock, there may be no need for the proximally-positioned locking mechanism. Such an embodiment can allow a user to lock the unexpanded fastener to the suture line, and then expand the fastener as a separate step.

Figure 7B:
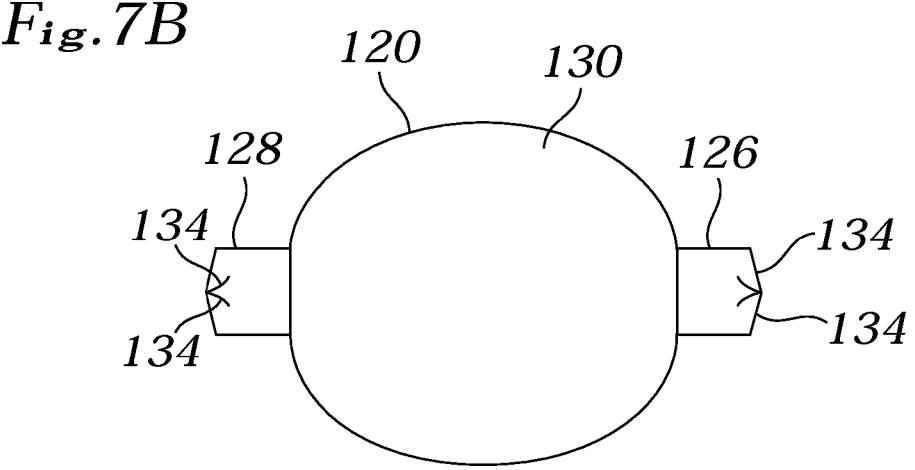
FIG. 7B depicts a side view in cross section of a fastener according to an embodiment of the invention.

FIG. 7B depicts a further embodiment of the fastener 120, but with locking teeth 134a, 134b in both the distal and proximal sections 126, 128, respectively. Such an embodiment can allow a user to lock the unexpanded fastener to the suture line using the distal lock, and then expand the fastener as a separate step. The proximal lock can then be secured to reinforce the lock on the suture lines and/or to maintain the fastener in the expanded configuration.

Figure 8A:
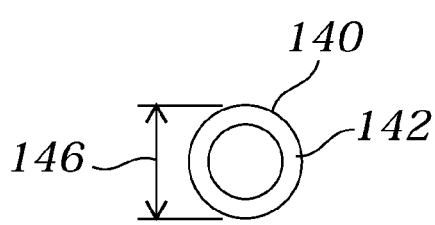
FIGS. 8A and 8B end and side views, respectively, of a fastener in the unexpanded condition according to an embodiment of the invention.
Figure 8B:
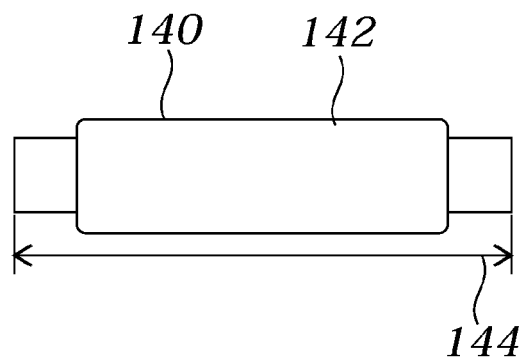
Figure 8C:
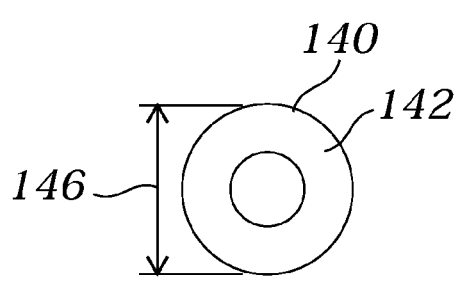
FIGS. 8C and 8D depict end and side views, respectively, of the fastener from FIGS. 8A and 8B in the expanded condition according to an embodiment of the invention.
Figure 8D:
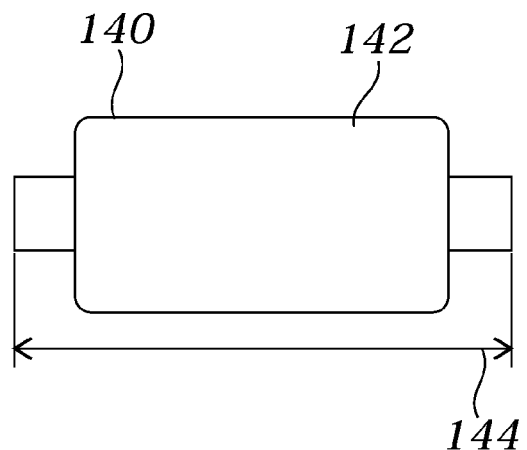
Figure 9A:
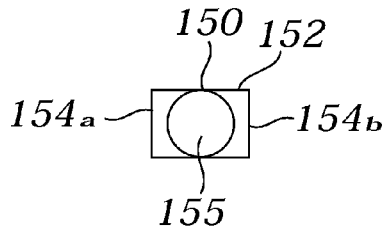
FIGS. 9A, 9B, and 9C depict end, side, and top views, respectively, of a fastener in the unexpanded condition according to an embodiment of the invention.
Figure 9B:
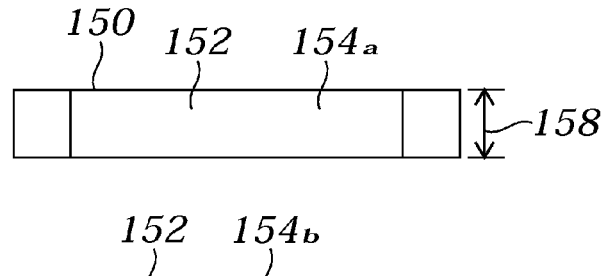
Figure 9C:
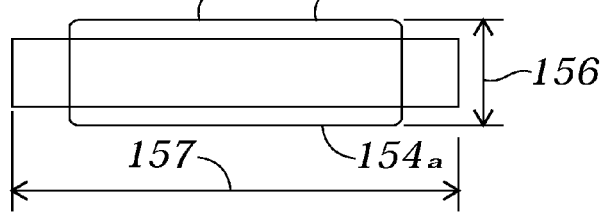
Figure 9D:
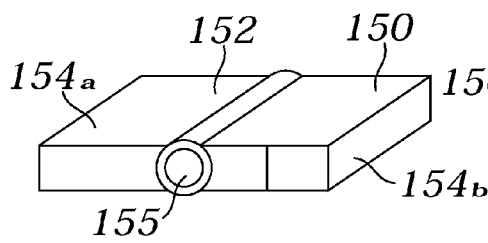
FIGS. 9D, 9E, 9F, and 9G depict perspective, side, end, and top views, respectively, of the fastener from FIGS. 9A, 9B, and 9C in the expanded condition according to an embodiment of the invention.
Figure 9E:
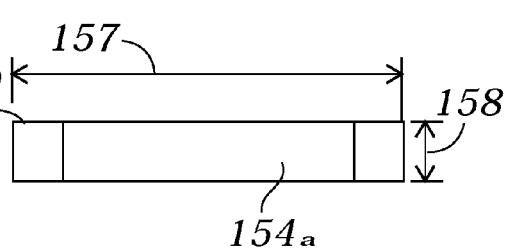
Figure 9F:
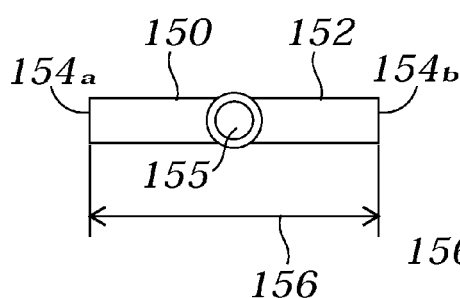
Figure 9G:
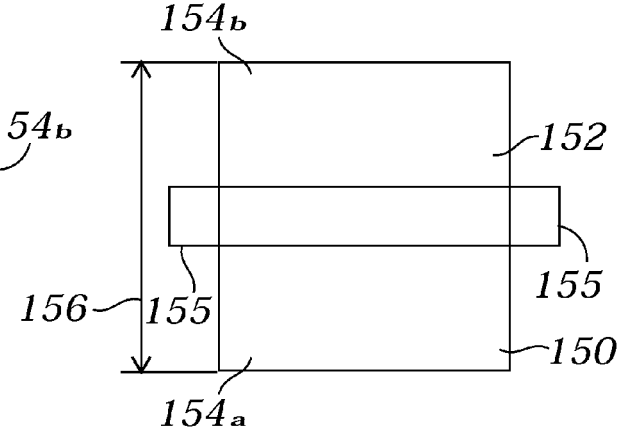

In the embodiments of FIGS. 6D-6E through 7B, the expandable section assumed a generally spherical shape upon expansion. However, other shapes are also within the scope of the invention, depending on the particular application. For example, FIGS. 8A-8D depict a fastener 140 with an expandable section 142 that is generally cylindrical in both its unexpanded state (FIGS. 8A-8B) and also in its expanded state (FIGS. 8C-8D). In the particular embodiment depicted, the fastener length 144 remains relatively constant during expansion, while the fastener outside diameter 146 increases. Such an expanded cylindrical shape may be suitable for advancement and expansion within a tunnel-like opening, and may be particularly suited for closure of PFO's and other openings having generally tunnel-like shapes.

FIGS. 9A-9G depict a fastener 150 having an expandable section 152 with two wing-like expansion sections 154a, 154b on either side of the expandable section 152. A suture lumen 155 runs along the length of the fastener. In the unexpanded state (FIGS. 9A-9C), the fastener 150 is generally cylindrical, but has slight bulges along the sides of the expandable section 152 caused by the unexpanded wing-like sections 154a, 154b. When expanded (FIGS. 9D-9G), the length 157 and height 158 of the fastener 150 remain largely unchanged, while the width 156 increases substantially. The fastener 150 thus assumes a generally flattened shape, with a width 156 that is substantially larger than its height 158.

In addition to the spherical, cylindrical, and generally flat fastener shapes discussed above, other expanded fastener shapes are also within the scope of the invention, depending on the particular application.

FIGS. 10A-10D depict a further embodiment of a fastener 160, wherein the expandable portion 162 is an expandable cage formed from deformable struts 164. The deformable struts 164 can be formed from various materials, including metals, plastics, and other biocompatible materials. The deformable struts 164 could be formed from elastically deformable materials, plastically deformable materials, and/or memory materials such as Nitinol. The fastener 160 has a length 166 and outside diameter 168 which vary during expansion.

Figure 10A:
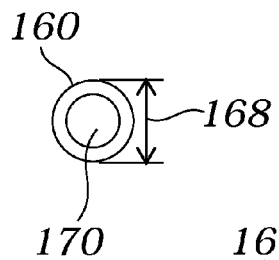
FIGS. 10A and 10B depict end and side views, respectively, of a fastener in the unexpanded condition according to an embodiment of the invention.
Figure 10B:
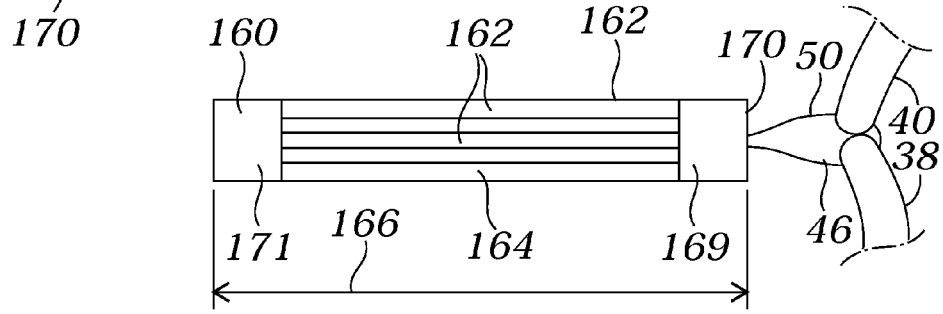
Figure 10C:
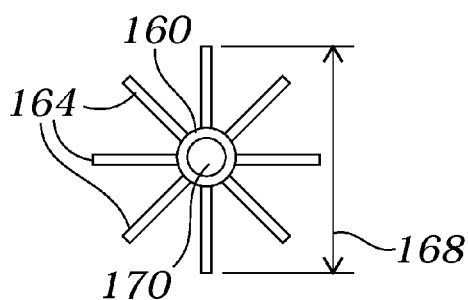
FIGS. 10C and 10D depict end and side views, respectively, of the fastener from FIGS. 10A and 10B in the expanded condition according to an embodiment of the invention.
Figure 10D:
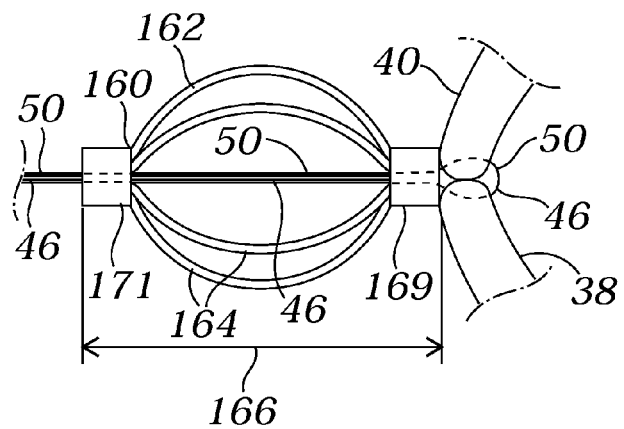

In FIGS. 10A-10B, the fastener 160 is in its unexpanded configuration, with the deformable struts 164 generally straight and aligned in parallel configuration about the radius of the expandable portion 162. The suture lumen 170 is unobstructed so that the suture lines 46, 50 can pass easily therethrough. In FIGS. 10C-10D, the fastener 160 is expanded into a generally spherical cage-like shape, with the deformable struts 164 each deforming generally equally along it length to form a generally semi-circular arc shape. The fastener length 166 has shortened, while the fastener diameter 168 has increased. Depending on the particular application, this spherical shape can be the final expanded shape of the fastener 160 during deployment. The fastener 160 can be secured to the suture lines 46, 50 via one or more suture locks (not shown), which could be positioned in the distal portion 169, proximal portion 171, or elsewhere in or on the fastener 160. The suture locks could comprise an inward flange, teeth, and/or other mechanism to block the suture lumen 170 or otherwise prevent the suture lines 46, 50 from passing through the fastener 160.

Figure 11A:
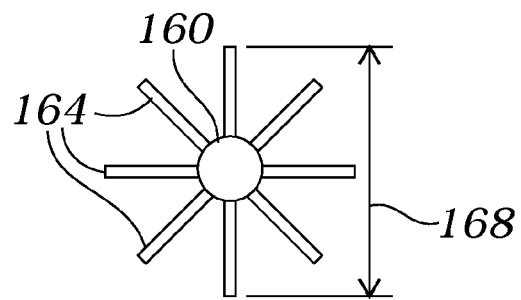
FIGS. 11A and 11B depict end and side views, respectively, of a fastener in the expanded condition according to an embodiment of the invention.
Figure 11B:
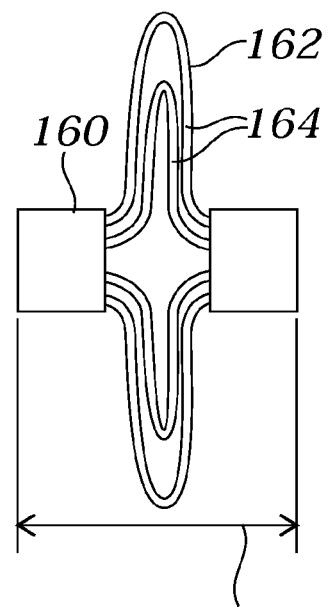

FIGS. 11A and 11B depict an additional expanded shape for a fastener clip 160 such as that depicted in the unexpanded configuration in FIGS. 10A-10B. The fastener clip 160 has been shortened further, so that the fastener length 166 is much less than the fastener diameter 168. The expandable portion 162 now forms a disk-like shape, generally flat when viewed from the side as in FIG. 11B and generally circular when viewed from the end as in FIG. 11A.

Figure 12:
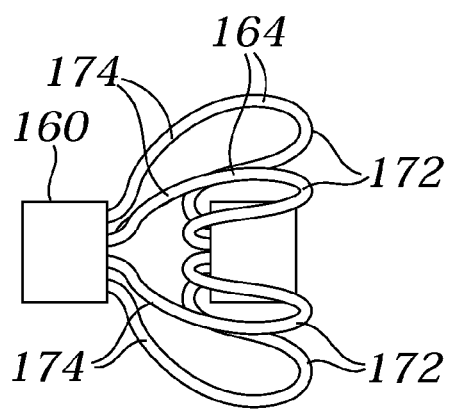
FIG. 12 depicts a side view of a fastener in the expanded condition according to an embodiment of the invention.

By using different materials in different portions of the expandable portion, a fastener can have other shapes upon expansion. FIG. 12 depicts a mushroom-like expanded shape for a fastener clip 160. Note that the fastener clip 160 has an unexpanded configuration similar to that depicted in FIGS. 11A-11C. The mushroom-like expanded shape could be achieved by forming the fastener 160 from memory materials such as Nitinol, and setting the mushroom-like shape as the preferred shape. Another approach for achieving the mushroom-like shape involves forming different portions of the expandable portion with different expansion characteristics. For example, different portions of the expandable struts could be formed from materials with different characteristics. The fastener 160 could be configured with the distal portions 172 of the struts 164 formed from material(s) that resist deformation less than the material(s) used to form the proximal portions 174 of the struts 164. As the fastener 160 expands radially and shortens lengthwise, the distal portions 172 will bend more than the proximal portions 174, resulting in a generally mushroom-like or conical shape. Note that the mushroom-like shape could be reversed to face the other direction by making the proximal portions more resistant to bending, etc.

Another method for providing different expanded shapes includes providing some strut portions (e.g., proximal portions) with greater thickness and/or width, which may inherently give those portions greater resistance to deformation. By making other strut portions (e.g., distal portions) with less thickness and/or width, the generally umbrella-like or conical shape discussed above, or other desired shapes, can be achieved.

Figure 13A:
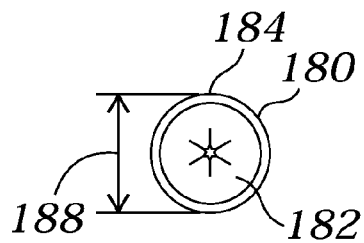
FIGS. 13A and 13B depict end and side views, respectively, of a fastener in the unexpanded condition according to an embodiment of the invention.
Figure 13B:
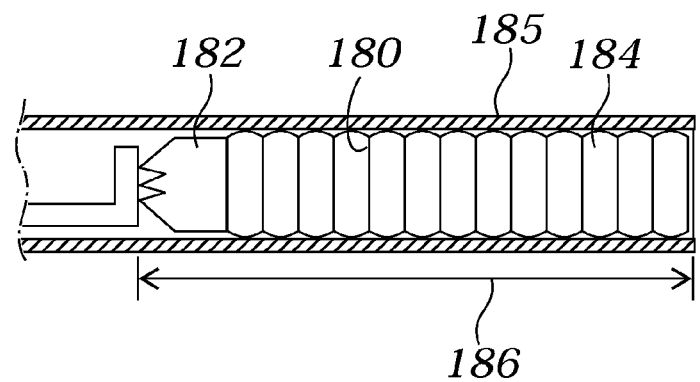
Figure 13C:
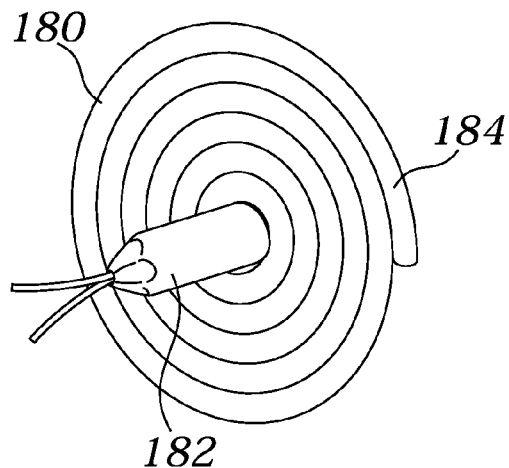
FIGS. 13C and 13D depict perspective and side views, respectively, of the fastener of FIGS. 13A-13B in the expanded condition according to an embodiment of the invention.
Figure 13D:
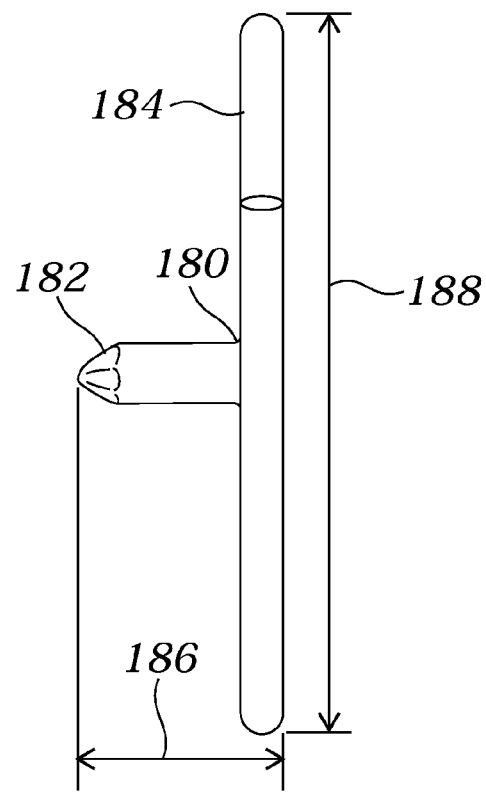
Figure 14A:
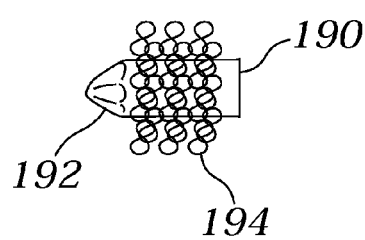
FIGS. 14A and 14B depict side and end views, respectively, of a fastener in the unexpanded condition according to an embodiment of the invention.
Figure 14B:
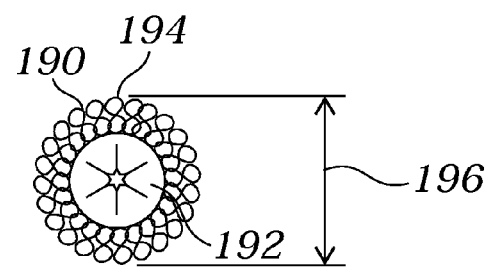
Figure 14C:
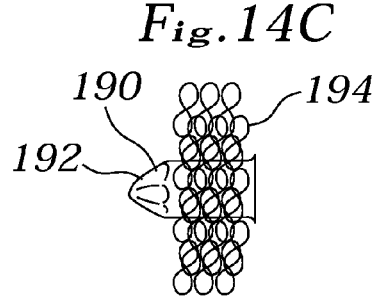
FIGS. 14C and 14D depict side and end views, respectively, of the fastener of FIGS. 14A-14B in the expanded condition according to an embodiment of the invention.
Figure 14D:
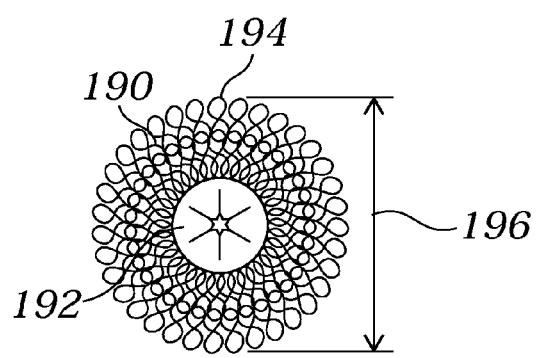

Another embodiment of an expandable fastener 180 is depicted in FIGS. 13A-13D, where the fastener 180 includes a locking clip 182 and expandable portion 184. The expandable portion 184 is a soft spiral spring, which could be formed from metal, polymers. In the unexpanded collapsed (compressed) state, such as where the fastener 180 is constrained by a catheter sheath 185 as depicted in FIGS. 13A-13B, the soft spiral spring of the expandable portion 184 assumes a coiled spring configuration, with the fastener 180 having a relatively large length 186 and relatively small diameter 188. When the fastener 180 is deployed, such as where the fastener 180 is pushed out of the surrounding sheath 185, the expandable portion 184 assumes an expanded generally circular geometry, as seen in FIGS. 143 and 143. The increased diameter 188 of the expandable portion 184 increases the sealing area of the fastener 180.

FIGS. 14A-14D depict a further embodiment of a fastener 190 with a locking clip 192 surrounded by an expandable coil 194 of bioresorbable material. In the delivery configuration (FIGS. 14A-14B), the diameter 196 of the expandable coil 194 is held to a relatively small size (which may be accomplished by a fastener catheter outer sheath (not shown) positioned around the fastener), but when expanded (FIGS. 14C-14D) the diameter 196 is substantially larger and serves to block the PFO opening and/or form a bridge over which tissue can grow. The bioresorbable material may have tissue-growth-inducing properties, and the surrounding tissue may grow over and absorb the bioresorbable material, thereby permanently closing the opening. Note that the locking clip 192 may also be bioresorbable, as may be the suture lines to which the fastener 190 is fastened, so that most or all of the repair assembly will be absorbed into the patient's body over time.

Figure 15A:
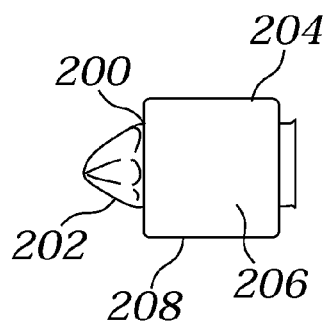
FIGS. 15A and 15B depict side and end views, respectively, of a fastener in the unexpanded condition according to an embodiment of the invention.
Figure 15B:
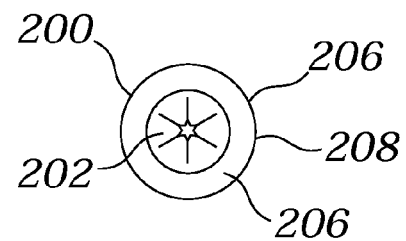
Figure 15C:
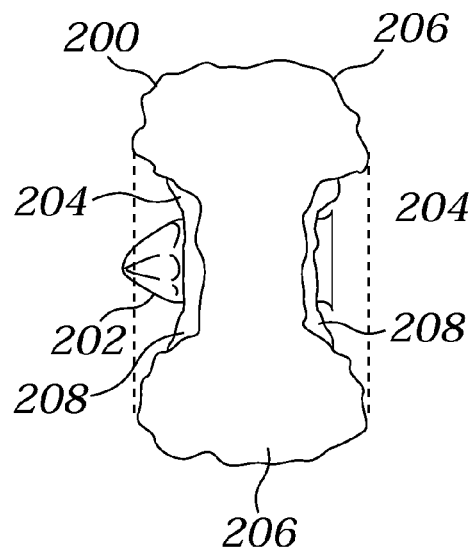
FIGS. 15C and 15D depict side and end views, respectively, of the fastener of FIGS. 15A-15B in the expanded condition according to an embodiment of the invention.
Figure 15D:
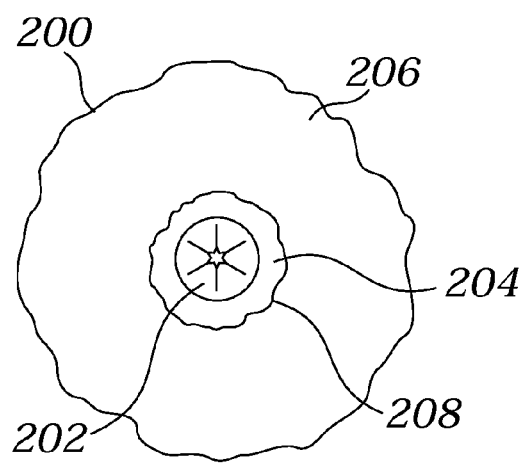

FIGS. 15A-15B depict a fastener 200 in delivery configuration having a locking clip portion 202 and a reservoir 204 of adhesive and/or foam-like material 206. Upon deployment (FIGS. 15C-15D), the reservoir 204 can rupture or otherwise open in order to release the adhesive and/or foam-like material 206, which expands around the locking clip portion 202 to block the PFO or other opening, and/or to adhere the surrounding tissue and/or fastener and/or suture together to close the opening. In an embodiment where the reservoir 204 ruptures, it may be desirable for the reservoir 204 to cleanly and predictably rupture so that the material forming the lining 208 of the reservoir 204 remains attached to the fastener 200. In another embodiment of the invention, the adhesive and/or foam-like material is discharged around the fastener from a reservoir or lumen on or in the fastener delivery catheter and/or another catheter. The fastener 200 may include a roughened outer surface and/or extending portions that form recesses and other surfaces to which the adhesive and/or foam-like material can expand around and/or adhere to.

Figure 16A:
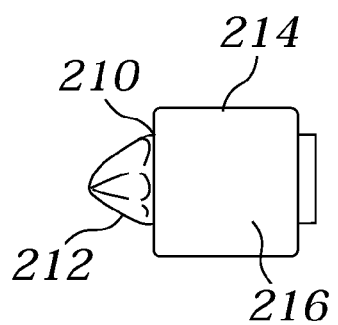
FIGS. 16A and 16B depict side and end views, respectively, of a fastener in the unexpanded condition according to an embodiment of the invention.
Figure 16B:
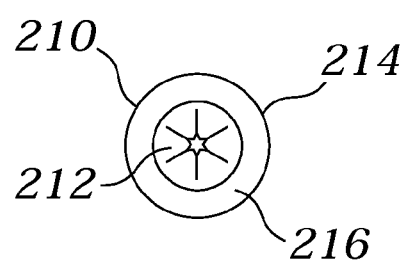
Figure 16C:
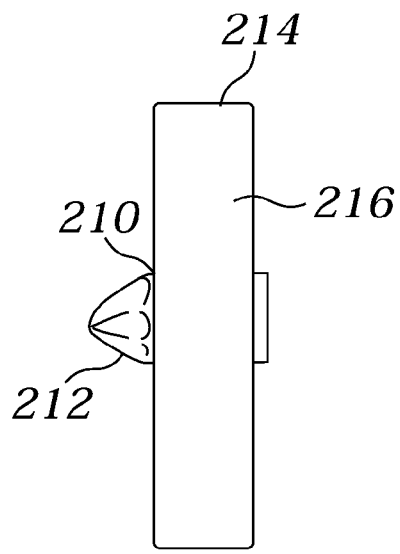
FIGS. 16C and 16D depict side and end views, respectively, of the fastener of FIGS. 16A-16B in the expanded condition according to an embodiment of the invention.
Figure 16D:
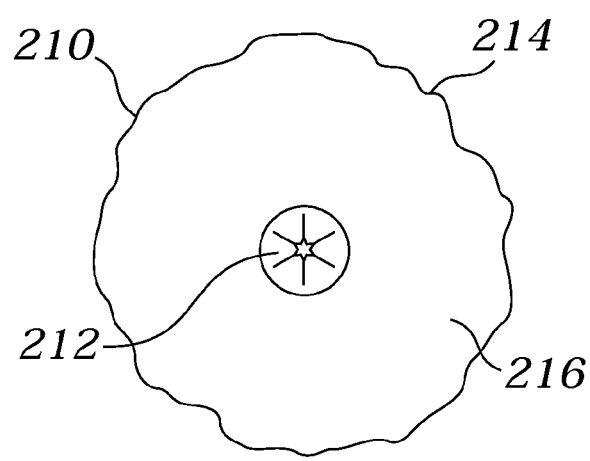

FIGS. 16A-16B depict a fastener 210 in delivery configuration having a locking clip portion 212 and an expandable portion 214 formed of an expandable sponge-like material 216 that expands when brought into contact with various materials, such as blood and/or other body fluids. The expandable sponge-like material 216 may be bioresorbable and/or tissue-growth-inducing. When the expandable portion 214 expands (FIGS. 16C-16D), which may occur gradually as the sponge-like material 216 absorbs fluids, the expandable portion 214 serves to block the PFO opening and/or form a bridge over which tissue can grow to block the opening.

Figure 17A:
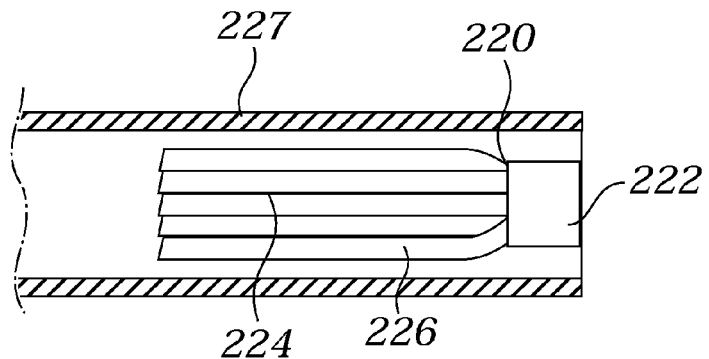
FIGS. 17A and 17B depict side and distal end views, respectively, of a fastener in the unexpanded condition according to an embodiment of the invention.
Figure 17B:
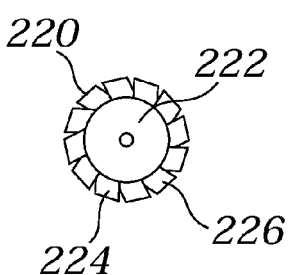
Figure 17C:
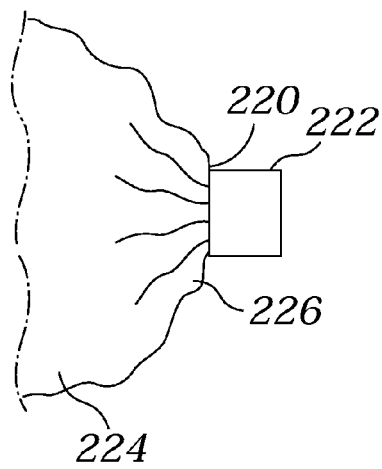
FIGS. 17C and 17D depict side and distal end views, respectively, of the fastener from FIGS. 17A and 17B in the expanded condition according to an embodiment of the invention.
Figure 17D:
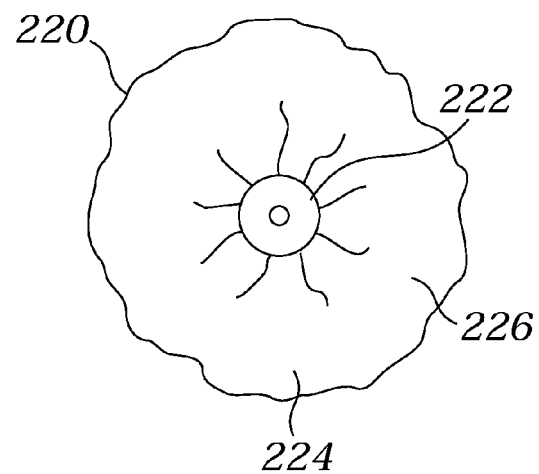

In another embodiment of the invention depicted in FIGS. 17A-17D, a fastener 220 includes a locking clip portion 222 and one or more plug portions 224 of plug and/or tissue-growth-inducing material. In the particular embodiment of FIGS. 17A-17D, a trailing plug portion 224 is a skirt of cloth 226. The cloth 226 may be a tissue-irritating material that will induce tissue ingrowth when brought into contact with tissue. In such an embodiment, the locking clip 222 is advanced into position and locked into place along the suture lines 46, 50 and adjacent the tissue portions 38, 40, as depicted in FIGS. 17A-17B. The trailing plug portion 224, which in the embodiment depicted in FIG. 17A was restrained by an outer sheath 227 of a delivery catheter, is then released to expand and/or spread out from the locking clip portion, as depicted in FIGS. 17C-17D, at which point the cloth 226 by its physical bulk helps to plug the PFO. The cloth 226 when released also comes into contact with the tissue. The tissue-irritating quality of the cloth 226 induces the tissue to grow over the cloth 226, which in time will further reinforce the closure of the PFO. Note that, depending on the particular opening and other deployment characteristics, the trailing cloth skirt 226 may not form the generally circular shape depicted in FIG. 18B, and may even be held tightly between tissue portions so that the trailing plug portion 224 is restrained into a very small size.

Figure 18A:
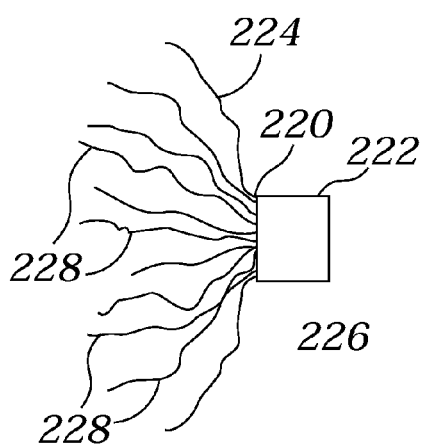
FIGS. 18A and 18B depict side and distal end views, respectively, of a fastener in the expanded condition according to an embodiment of the invention.
Figure 18B:
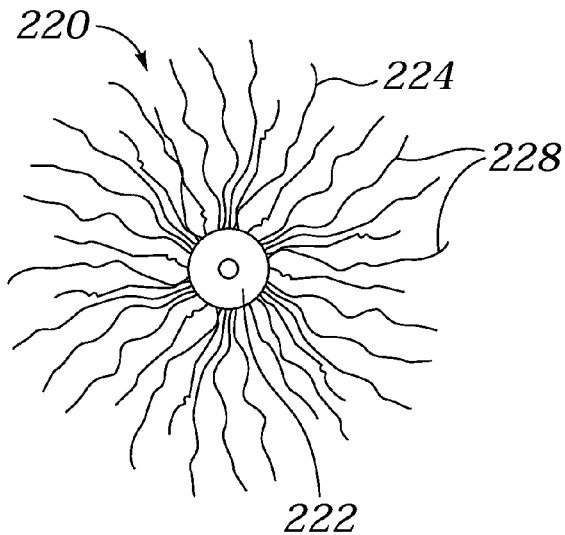

FIGS. 18A-18B depict a fastener 220 similar to that of FIGS. 17A-17D, except the trailing plug portion 224 comprises suture strands 228. The suture strands 228 may have tissue-irritating and growth-inducing properties. When the locking clip portion is locked into place on the suture lines adjacent tissue portions at or within a PFO or other opening, the trailing suture strands 228 may help to block the PFO by their bulk and/or by inducing the surrounding tissue to grow over the trailing suture strands. Note that FIGS. 18A and 18B depict the fastener 220 in the expanded condition. In the unexpanded condition, the suture strands 228 will be compressed to a much smaller diameter, similar to the manner in which the cloth skirt 226 was compressed in the embodiment of FIGS. 17A and 17B. When released from a restraint such as a catheter sheath, the trailing suture strands 228 can conform to the opening. Depending on the particular opening and other deployment characteristics, the trailing suture strands 228 may not form the generally circular shape depicted in FIG. 18B, and may even be held tightly between tissue portions so that the trailing plug portion 224 is restrained into a very small size.

The embodiments depicted in FIGS. 17A-17D and 18A-18B use trailing plug portions of materials, such as cloth and/or suture. However, the plug materials do not have to be positioned to trail behind the locking clip. For example, the plug materials (which may be tissue-growth-inducing materials) could be placed in front of, on the sides of, and/or all around the locking clip or other structures of the fastener. In addition to or in lieu of the cloth and suture depicted in FIGS. 17A-17D and 18A-18D, other materials could be used as plug materials. For example, microscopic PTFE fibers, which could be in the form of a pledget, may be attached to the fastener.

Figure 19A:
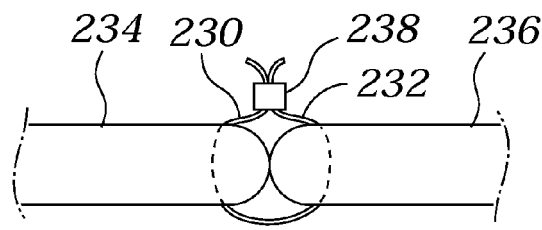
FIGS. 19A and 19B depict side views of suture used to securing tissue portions according to an embodiment of the invention.
Figure 19B:
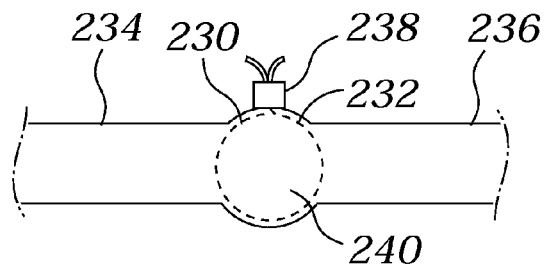

FIGS. 19A-19B depict a further embodiment of the invention, wherein first and second tissue-irritating suture lines 230, 232 themselves have enhanced tissue irritating qualities to induce tissue growth. For example, cat-gut suture, and/or suture having a generally rough or irritating surface (as opposed to the relatively smooth surface of most prolene sutures), and/or a suture containing or coated with chemicals having tissue-irritating and/or tissue-growth-inducing qualities, could be used in performing the repair. In FIG. 19A, the suture lines 230, 232 have recently been deployed through first and second tissue portions 234, 236, respectively, with a fastener 238 holding the suture lines 230, 232 firmly adjacent the tissue portions 234, 236. Note that in the embodiment depicted, the tissue portions 234, 236 are anterior and posterior leaflets, respectively, of a mitral valve. The surrounding tissue has not yet grown onto or into the suture lines 230, 232. In FIG. 19B, the surrounding tissue has grown over the suture lines 230, 232, forming a tissue bridge 240 between the first and second tissue portions 234, 236. Such tissue-irritating suture lines could be used in various procedures where an opening is desired to be closed. For example, in an edge-to-edge leaflet procedure conducted on a bicuspid mitral valve, a tissue-irritating suture line could be used to secure the first leaflet to the second leaflet. The tissue-irritant suture line would thus induce tissue formation over the resulting stitch, which would further reinforce the connection between the first leaflet and the second leaflet. The tissue-irritant suture line could be bioresorbable. The tissue-irritant suture line could also be used in combination with a tissue-irritant and/or bioresorbable fastener. Where a suture and/or fastener is bioresorbable, it may be preferred that the bioresorbability be configured so that the suture and/or fastener is not bioresorbed prior to formation of the tissue bridge of other tissue growth over the suture and/or fastener.

Figure 20A:
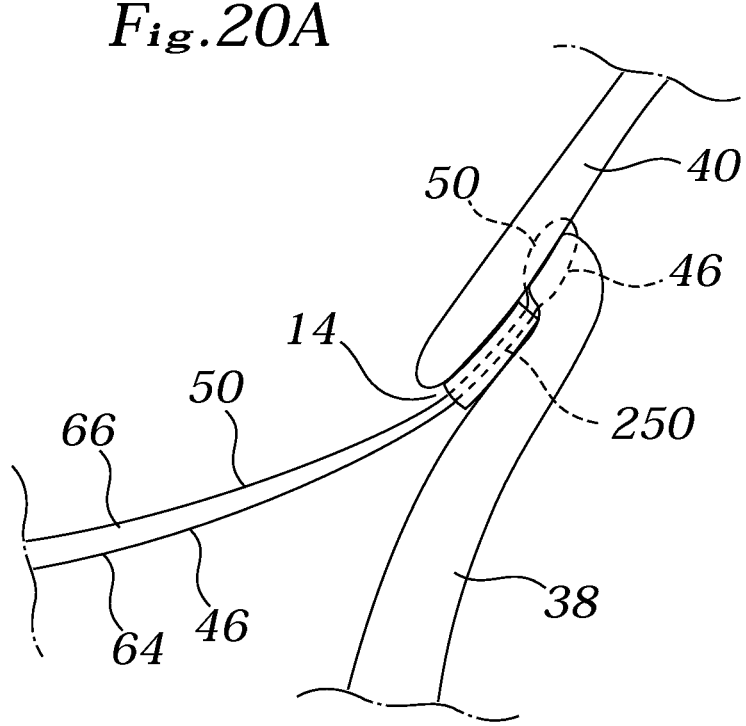
FIGS. 20A and 20B depict side views of one or more fasteners used to secure tissue according to an embodiment of the invention.
Figure 20B:
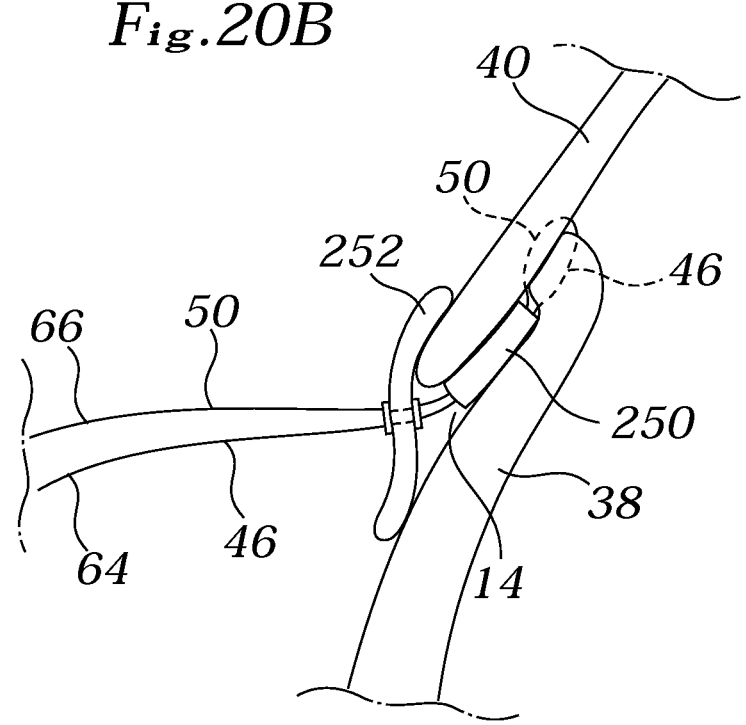

In a further embodiment of the invention, multiple fasteners can be employed, including multiple expandable and/or multiple unexpandable fasteners and various combinations thereof. For example, in FIG. 20A, a first fastener 250, which in the particular embodiment depicted is an expandable fastener, is deployed to secure the suture lines 46, 50 and tissue portions 38, 40 of a PFO 14. (Note, however, that an unexpandable fastener could instead be used as the first fastener.) The excess suture portion 64, 66 have not yet been removed, so that a user has the option of deploying additional fasteners along the suture lines 46, 50. Note that the first fastener 250 is deployed within the PFO itself. With the first fastener 250 deployed, the user can assess the efficacy of the repair using various assessment techniques, including visualization techniques such as fluoroscopy and/or echo. If the user can not confirm the completeness of the repair, the user can advance one or more additional fasteners along the suture lines 46, 50 to the repair site. In FIG. 20B, the user has delivered and deployed a second fastener 252, which in the particular embodiment depicted is an expandable fastener. Note that the second fastener is a generally disk-shaped fastener and is positioned adjacent the proximal opening of the PFO instead of within the PFO. With the second fastener 252 in position and expanded, the user can again assess the efficacy of the repair, and if desired can add additional fasteners. Once the user is satisfied with the repair, the user will cut and remove the excess suture portions 64, 66, leaving the fasteners (e.g., 250, 252) in place to hold the tissue 38, 40 together.

Figure 21A:
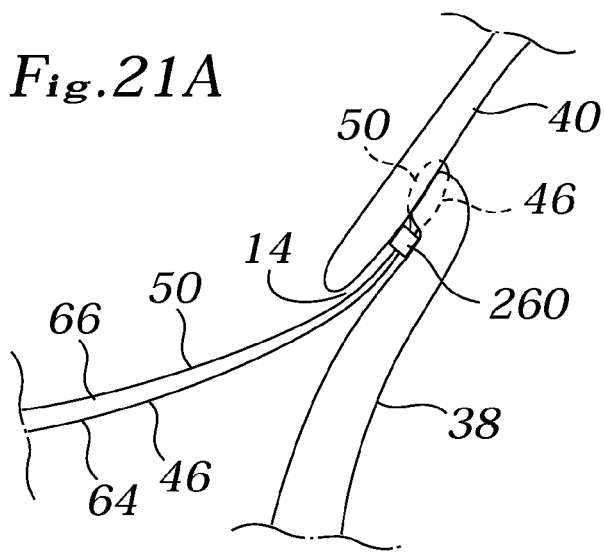
FIGS. 21A, 21B, and 21D depict side views of plugs and fasteners used to secure tissue according to an embodiment of the invention.
Figure 21B:
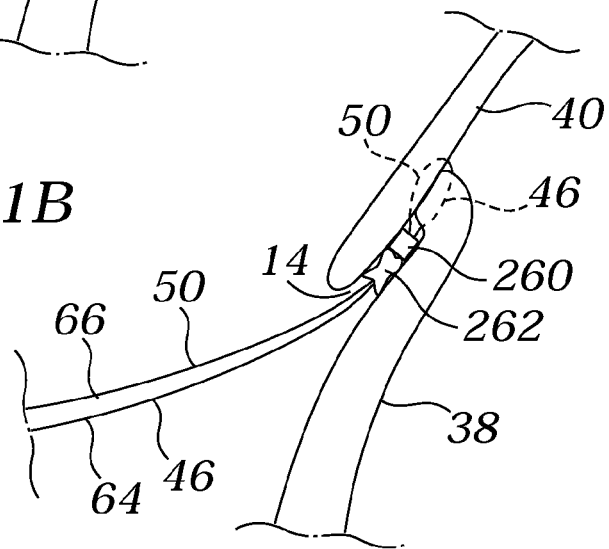
Figure 21C:
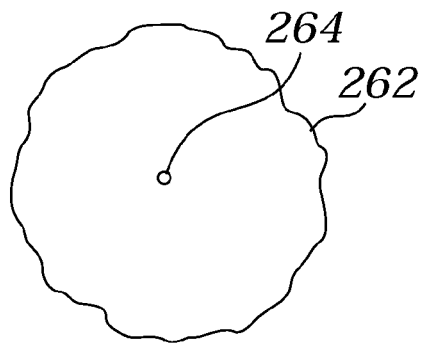
FIG. 21C depicts a front view of the plug from FIGS. 21B and 21D.

In another embodiment of the invention, one or more locking fasteners are used with intervening expandable portions and/or other plug materials to close a PFO. In FIG. 21A, the user has delivered and deployed a first fastener 260 on sutures lines 46, 50 in a PFO 14. In the particular embodiment depicted, the fastener 260 is an unexpandable fastener; however, an expandable fastener could instead be used as a first-deployed fastener. With the first fastener 260 deployed, the user can assess the efficacy of the repair using various assessment techniques, including visualization techniques such as fluoroscopy and/or echo. If the user desires (e.g., if the user can not confirm the completeness of the repair), the user can advance one or more plugs along the suture lines 46, 50 to the repair site. (Note that, if the user desires, one or more plugs may be advanced along the suture lines to the PFO prior to or simultaneously with placement of the first fastener at the PFO.) In FIG. 21B, a plug 262, which in the particular embodiment depicted is a piece of tissue-irritating cloth, has been advanced along the suture lines 46, 50 until the plug 262 is adjacent the first fastener 260 and the tissue portions 38, 40. The plug 262, depicted in front view in FIG. 21C, has a central opening 264 through which the suture lines 46, 50 can pass. The central opening 264 may preferably be a bounded opening so that the suture lines 46, 50 cannot slip sideways through the plug 262 (i.e., can only pass longitudinally through the plug 262 through the central opening 264), which will prevent the plug from sliding sideways off of the suture lines 46, 50. The central opening 264 may also be sized and configured so that the sutures 46, 50 can pass therethrough but a fastener deployed proximally of the plug 262 will not slip through the plug central opening 264.

Figure 21D:
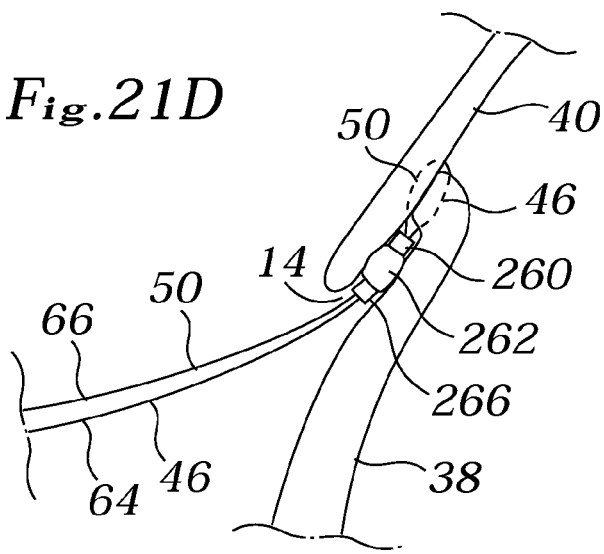

A second fastener 266 (which in the particular embodiment depicted is an unexpandable fastener) is advanced along the suture lines 46, 50 until it is seated and locked into position against the plug 262. The plug 262 is thus held firmly on the suture lines 46, 50 between the first and second fasteners 260, 266, as depicted in FIG. 21D. Additional plugs and fasteners can be deployed until the PFO is securely closed or the user is otherwise satisfied with the repair. After all plugs and fasteners are deployed, the user will cut and remove the excess suture portions 64, 66 of sutures 46, 50.

Note that one or more plugs can be deployed along the suture lines prior to deployment of the first fastener, with the first fastener positioned and secured to the suture lines proximally of the plug or plugs. In one such embodiment, a first plug is advanced to the treatment site and held against the tissue portions (which may be accomplished with a plug and/or fastener delivery catheter) while the user assesses the efficacy of the repair using methods such as fluoroscopy, etc. If the user desires, the user can advance additional plugs to the repair site until the user is satisfied with the repair, then advance a fastener clip to hold the plug or plugs firmly in place against the tissue portions to complete the repair. In such an embodiment, the plug or plugs will be held firmly on the suture lines, sandwiched between the tissue portions and the first fastener. The deployment of multiple plugs with a single fastener can be part of a single fastener deployment, or as a combination of multiple plugs and multiple fasteners such as that described above with respect to FIGS. 21A-D.

Figure 22A:
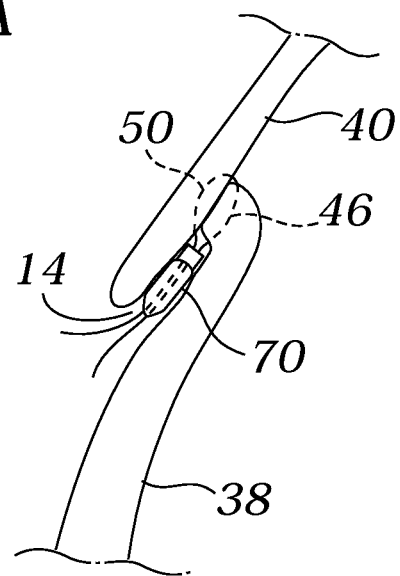
FIG. 22A depicts a side view of a fastener deployed within a PFO according to an embodiment of the invention.
Figure 22B:
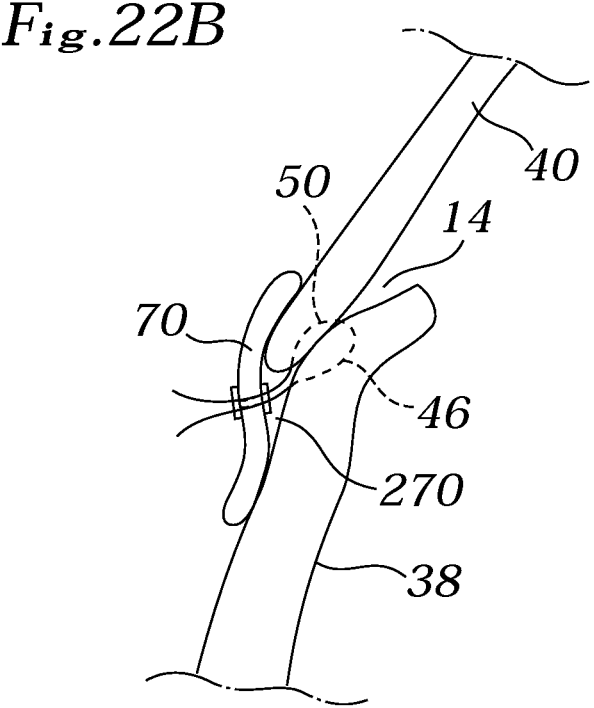
FIG. 22B depicts a side view of a fastener deployed adjacent a PFO according to an embodiment of the invention.

The invention includes various placements of the suture lines, fasteners, and/or plugs with respect to the PFO or other treatment site. In one embodiment depicted in FIG. 22A, the suture lines 46, 50 are deployed in a distal area of the PFO 14, and a fastener 70 is advanced and deployed within the PFO 14 itself. In another embodiment depicted in FIG. 22B, a fastener 70 is deployed and expanded adjacent the proximal opening 270 of the PFO 14, so that the fastener 70 presents a generally flat surface that presses against (and may conform to) the tissue surrounding the proximal opening 270 of the PFO. The fastener 70 thus serves as a lid-like closure on the PFO 14. Note that the selection of a particular fastener used for a particular procedure may depend on the desired deployment characteristics. A generally flat disk-like fastener may be desirable to form a lid-like closure such as that depicted in FIG. 22B, while an expanding plug of tissue-growth-inducing material may be desirable for a plug-like closure within the PFO such as that depicted in FIG. 22A.

Note that the fasteners of the invention can have various configurations and/or be formed of various materials. For example, a fastener locking clip, expandable portion, and/or plug portion could be formed from various materials and combinations thereof, including foam-like structures, cloth, coils, tissue-irritating materials that will induce tissue ingrowth, bioresorbable materials, etc. Various dimensions of the fastener could be altered to suit a particular application. For example, the suture lumen does not necessarily have to be shaped having a length greater than the diameter, and instead of a long suture lumen the suture could instead pass through any opening in the clip configured to slidingly receive at least one line of suture. The suture of the invention could also have various characteristics, including bioresorbability and/or tissue-growth-inducing properties.

While the invention has been described with reference to particular embodiments, it will be understood that various changes and additional variations may be made and equivalents may be substituted for elements thereof without departing from the scope of the invention or the inventive concept thereof. For example, while the invention has been discussed in detail in the application with repair of septal defects such as PFOs, it has applicability in other areas where it is desired to repair tissue and/or close openings. For example, the invention may be used to close body lumens and/or openings, including a left atrial appendage, or in so-called edge-to-edge mitral valve repairs, etc. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A method of treating a septal defect between a first heart chamber and a second heart chamber in a heart of a patient, comprising:
    advancing a suturing catheter through a circulatory pathway to a location in the first heart chamber of the heart proximate to the septal defect;
    deploying a first suture portion into a first tissue portion adjacent the septal defect;
    deploying a second suture into a second tissue portion adjacent the septal defect;
    withdrawing the suturing catheter from the patient while leaving the first suture portion and the second suture portion extending from the septal defect through the first heart chamber and to a position outside of the patient;
    advancing a first septal closure device along the first suture portion and the second suture portion from a position outside the patient to a position adjacent the septal defect, wherein the first septal closure device comprises a first septal closure device suture lumen and the first septal closure device is advanced with the first and second suture portions sliding within the first septal closure device suture lumen;
    deploying the first septal closure device at a position adjacent or within the septal defect;
    after advancing the first septal closure device to a position adjacent or within the septal defect, advancing a second septal closure device along the first suture portion and the second suture portion from a position outside the patient to a position adjacent the first septal closure device, wherein the second septal closure device comprises a second septal closure device suture lumen and the second septal closure device is advanced with the first and second suture portions sliding within the second septal closure device suture lumen;
    cutting and removing the excess suture leading from the septal defect to the position outside of the patient, wherein after removal of the excess suture no portion of any closure device or other device deployed during the procedure other than the suture line itself is positioned within the second heart chamber, wherein the first septal closure device comprises a suture clip, and the second septal closure device comprises an expandable plug member; and
    expanding the expandable plug member adjacent or within the septal defect.

2. The method of claim 1, further comprising:
    prior to advancing the suturing catheter to the septal defect, advancing a guide catheter through a circulatory pathway to a location in the heart proximate to the septal defect;
    wherein advancing a suturing catheter to a position adjacent the septal defect comprises advancing a suturing catheter through the guide catheter.

3. The method of claim 1, wherein the first suture portion and the second suture portion comprise adjacent portions of a single continuous length of suture.

4. The method of claim 3, further comprising:
    after passing the first suture portion through the first tissue portion and passing the second suture portion through the second tissue portion, the further step of tightening the first and second suture portions and thereby drawing the first and second tissue portions together.

5. The method of claim 1, comprising:
after advancing the first septal closure device along the first suture portion to the position adjacent the septal defect, but before advancing the second septal closure device to a position adjacent the first septal closure device, the further step of assessing the efficacy of the septal repair.

6. A method of treating a patent foramen ovale in a patient's heart, the method comprising:
providing a suture catheter having a proximal end and a distal end;
advancing the suture catheter through the patient's circulatory system to position the distal end within the patent foramen ovale;
passing a suture line through a septum primum of the patent foramen ovale;
passing the suture line through a septum secundum of the patent foramen ovale;
withdrawing the suture catheter while leaving the suture line trailing from the patent foramen ovale to a position outside of the patient;
advancing a first patent foramen ovale closure device from a position outside the patient over the suture line to a position within the patent foramen ovale such that the first patent foramen ovale closure device is sandwiched between the septum primum and the septum secundum;
after advancing the first patent foramen ovale closure device from a position outside the patient over the suture line to a position within the patent foramen ovale, advancing a second patent foreman ovale closure device along the first suture portion and the second suture portion from a position outside the patient to a position adjacent the first patent foramen ovale closure device;
cutting excess suture from the suture lined trailing from the patent foramen ovale to the position outside of the patient while leaving the portions of the suture line which pass from the first patent foramen ovale closure device through the septum primum and through the septum secundum and back to the first patent foramen ovale closure device;
wherein after the step of cutting excess suture from the first and second suture portions leading from the first patent foramen ovale closure device to the position outside of the patient, no portion of any closure device or other device deployed during the procedure other than the suture line itself is positioned within the left atrium; and
after advancing the second patent foramen ovale closure device from a position outside the patient over the suture line to a position adjacent the first patent foramen ovale closure device, but before cutting excess suture from the first and second suture lines, advancing a third patent foreman ovale closure device along the first suture portion and the second suture portion from a position outside the patient to a position adjacent the second patent foramen ovale closure device, such that the second patent foramen ovale closure device is sandwiched between the first patent foramen ovale closure device and the third patent foramen ovale closure device.

7. The method of claim 6, further comprising:
tightening the suture line and thereby drawing together the septum primum and septum secundum.

8. The method of claim 7, wherein the catheter device comprises a first vacuum recess, and further comprising:
applying a vacuum to the first vacuum recess to stabilize the septum primum.

9. The method of claim 8, wherein the catheter device comprises a second vacuum recess, and further comprising:
applying a vacuum to the second vacuum recess to stabilize the septum secundum.

10. The method of claim 9, wherein applying the vacuum to the first vacuum recess occurs simultaneously with applying the vacuum to the second vacuum recess.

11. The method of claim 9, wherein applying the vacuum to the first vacuum recess occurs before applying the vacuum to the second vacuum recess.

12. The method of claim 6, wherein the first patent foramen ovale closure device comprises a suture clip.

13. The method of claim 6, wherein the second patent foramen ovale closure device comprises a suture clip.

14. The method of claim 6, wherein the first patent foramen ovale closure device comprises an expandable plug member.

15. The method of claim 6, wherein the first patent foramen ovale closure device comprises a suture clip, the second patent foramen ovale closure device comprises an expandable plug, and the third patent foramen ovale closure device comprises a suture clip.

* * * * *